US012788613B2

(12) United States Patent
Kim

(10) Patent No.: US 12,788,613 B2
(45) Date of Patent: Nov. 10, 2026

(54) PANTS FOR URINE OR FECES AND METHOD OF DISPOSING OF URINE AND FECES

(71) Applicant: Who Young Kim, Icheon-si Gyeonggi-do (KR)

(72) Inventor: Who Young Kim, Icheon-si Gyeonggi-do (KR)

( * ) Notice: Subject to any disclaimer, the term of this patent is extended or adjusted under 35 U.S.C. 154(b) by 609 days.

(21) Appl. No.: 18/297,435

(22) Filed: Apr. 7, 2023

(65) Prior Publication Data

US 2023/0310202 A1 Oct. 5, 2023

Related U.S. Application Data

(63) Continuation of application No. PCT/KR2023/003243, filed on Mar. 9, 2023.

(30) Foreign Application Priority Data

Mar. 30, 2022 (KR) ........................ 10-2022-0039289
Aug. 23, 2022 (KR) ........................ 10-2022-0105283
Feb. 20, 2023 (KR) ........................ 10-2023-0021917

(51) Int. Cl.

| | |
|---|---|
| ***A61F 5/44*** | (2006.01) |
| ***A41D 13/00*** | (2006.01) |
| ***A61F 5/441*** | (2006.01) |
| ***A61F 5/442*** | (2006.01) |
| ***G01N 21/55*** | (2014.01) |

(52) U.S. Cl.

CPC ............ *A61F 5/4408* (2013.01); *A41D 13/00* (2013.01); *A61F 5/441* (2013.01); *A61F 5/442* (2013.01); *G01N 21/55* (2013.01)

(58) Field of Classification Search

CPC ........ A61F 5/4408; A61F 5/441; A61F 5/442; A61F 5/44; A61F 5/451; A61F 13/42; A61F 13/49; A61F 13/495

See application file for complete search history.

(56) References Cited

U.S. PATENT DOCUMENTS 6,167,578 B1 * 1/2001 Kitamura ............... A61H 35/00 4/456

FOREIGN PATENT DOCUMENTS

| | | | | |
|---|---|---|---|---|
| CN | 113081452 A * | 7/2021 | ......... | A61G 7/05769 |
| EP | 0494488 A1 * | 7/1992 | ............... | A61G 9/00 |
| KR | 20220060295 A * | 5/2022 | ............... | A61G 9/02 |

* cited by examiner

*Primary Examiner* — Jessica Arble
*Assistant Examiner* — Hans Kaliher

(57) ABSTRACT

Pants (diaper) for urine or feces capable of disposing of urine or feces several times in a sanitary condition are disclosed. The pants for urine/feces comprises a pants member configured to have an internal space, a space division member connected to the pants in the internal space, thereby dividing the internal space into a first space and a second space and an expansion section disposed in the second space. Here, a hip of a user or the hip and a thigh locate in the first space, the hip or the hip and the thigh are lifted when the expansion section is expanded in the second space to form a space for urine/feces where the urine/feces is collected.

24 Claims, 24 Drawing Sheets

PANTS FOR URINE OR FECES AND METHOD OF DISPOSING OF URINE AND FECES

CROSS-REFERENCE TO RELATED APPLICATIONS

This application is a Bypass Continuation of pending PCT International Application No. PCT/KR2023/003243, which was filed on Mar. 9, 2023, and which claims priority from and the benefit of Korean Patent Application No. 10-2022-0039289, filed on Mar. 30, 2022, Korean Patent Application No. 10-2022-0105283, filed on Aug. 23, 2022, and Korean Patent Application No. 10-2023-0021917, filed on Feb. 20, 2023, respectively, in the Korean Intellectual Property Office, all of which are hereby incorporated by reference for all purposes as if fully set forth herein. In addition, when this application also claims priority for countries other than the United States for the same reason as above, all of the contents of the above-listed applications are hereby incorporated by reference.

TECHNICAL FIELD

The disclosure relates to pants for urine/feces and method of disposing of urine and feces.

BACKGROUND ART

Most of patients or old men in a nursing hospital can't move very well. Hence, family member or caregiver disposes of urine or feces of the patient while the patient is lying abed.

Particularly, the family member or the caregiver takes off a disposal diaper from the patient when the patient relieves oneself, and then he puts the patient on new diaper. This diaper exchanging process is performed several times a day.

The caregiver exchanges the diaper of the patient because the family member can't care the patient during the daytime, but it is difficult to exchange the diaper at a proper time due to lack of the caregiver. Accordingly, sanitary condition of the patient may not be good.

Additionally, since a diaper for urine and a diaper for feces exist separately, a good many diapers are used a day. As a result, environmental pollution may occur according as many diapers are dumped.

SUMMARY

To solve problem of the convention technique, the disclosure is to provide pants (diaper) for urine/feces capable of disposing of urine/feces several times in a sanitary condition.

A pants for urine or feces according to an embodiment of the disclosure includes a pants member configured to have an internal space; a space division member connected to the pants in the internal space, thereby dividing the internal space into a first space and a second space; and an expansion section disposed in the second space. Here, a hip of a user or the hip and a thigh locate in the first space, the hip or the hip and the thigh are lifted when the expansion section is expanded in the second space to form a space for urine/feces where the urine/feces is collected.

A pants for urine/feces according to another embodiment of the disclosure comprises a pants member configured to have an internal space; an expansion section disposed in the pants member; and a light sensor located in the pants member. Here, a hip or the hip and a thigh of a user is lifted when the expansion section is expanded, thereby forming a space for collecting the urine/feces, a light sensor senses a light reflected by the collected urine/feces or contaminated water or a light through the collected urine/feces or the contaminated water, and it is detected through the sensed result whether or not the user discharges the urine/feces.

A pants for urine/feces according to still another embodiment of the disclosure comprises a first sub pants in which a body of a user is inserted; a second sub pants connected to the first sub pants and configured to have an internal space; and an expansion section included in the second sub pants. Here, wherein a hip or the hip and a thigh are lifted when the expansion section is expanded in the second sub pants, thereby forming a space for urine/feces in which the urine/feces is collected in the first sub pants.

Pants (diaper) for urine/feces according to an embodiment of the disclosure may dispose of urine/feces several times and be reused after it is cleaned, and so environmental pollution may reduce.

In the pants for urine/feces, a space for collecting urine/feces is generated according as a hip is lifted, and thus a phenomenon that the urine/feces in the space is contacted with his skin may be minimized.

BRIEF DESCRIPTION OF DRAWINGS

Example embodiments of the present invention will become more apparent by describing in detail example embodiments of the present invention with reference to the accompanying drawings, in which.

DETAILED DESCRIPTION

In the present specification, an expression used in the singular encompasses the expression of the plural, unless it has a clearly different meaning in the context. In the present specification, terms such as “comprising” or “including,” etc., should not be interpreted as meaning that all of the elements or operations are necessarily included. That is, some of the elements or operations may not be included, while other additional elements or operations may be further included. Also, terms such as “unit,” “module,” etc., as used in the present specification may refer to a part for processing at least one function or action and may be implemented as hardware, software, or a combination of hardware and software.

The disclosure relates to a diaper for old man or patient (user), specifically a diaper for nursing hospital, and the diaper may dispose of urine/feces several times. Accordingly, it releases inconvenience of exchanging frequently the diaper and urine/feces may be easily disposed of.

In an embodiment, the diaper of the disclosure may make a space for collecting urine/feces when user’s urine/feces is sensed, remove immediately urine/feces collected in the space and clean a hip of the user on which the feces is stained. This diaper may be reused after washed.

Specially, the space is formed to minimize contact of urine/feces collected in the space and the user’s skin, and so it is hygienic.

Most of patients or old men in the nursing hospital can’t move very well, and thus they relieve themselves while they are lying abed. As a result, family member or caregiver exchanges a disposable diaper several times a day, wherein the disposable diaper may contaminate environment.

Additionally, since a diaper for urine and a diaper for feces exist separately, the diaper for urine and the diaper for feces should be changed apart. The diaper of the patient is not smoothly exchanged due to lack of the caregiver, and so sanitary condition of the patient may not be good.

To solve this problem, the disclosure provides a diaper capable of disposing of urine/feces several times in a sanitary condition.

Hereinafter, various embodiments of the invention will be described in detail with reference to accompanying drawings. It is assumed that patient uses the diaper, for the purpose of convenience of description.

Figure 1:
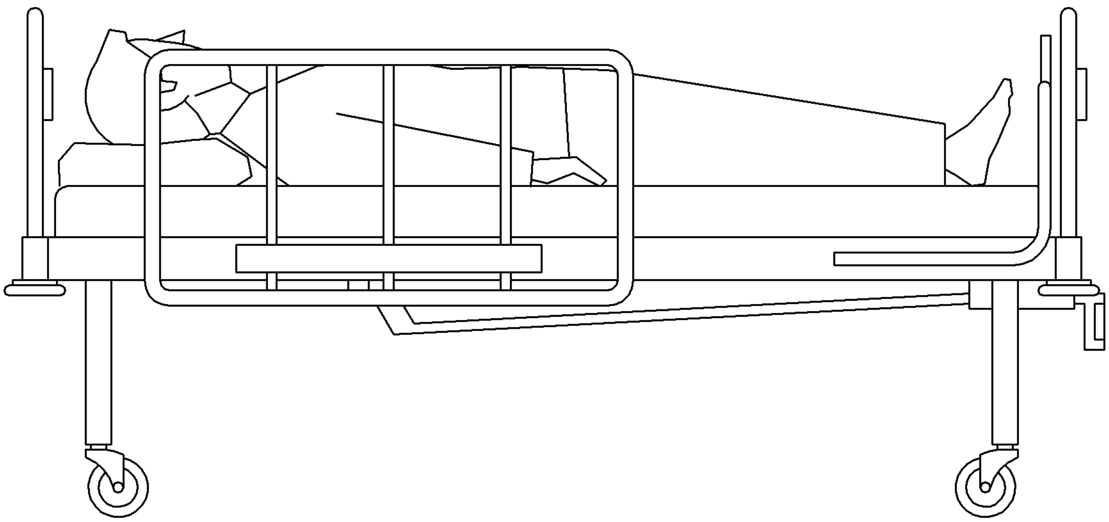
FIG. 1 is a view illustrating patient lying on a bed.
Figure 2:
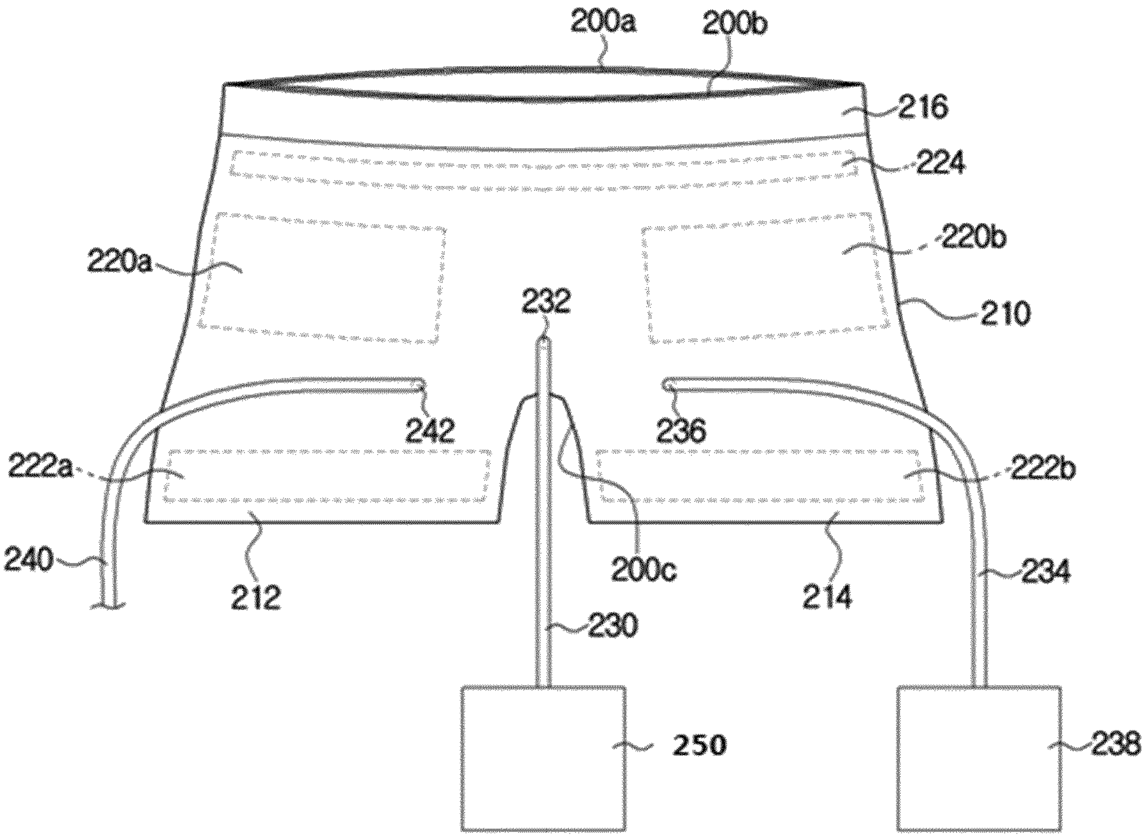
FIG. 2 is a view illustrating a diaper according to an embodiment of the invention.
Figure 3A:
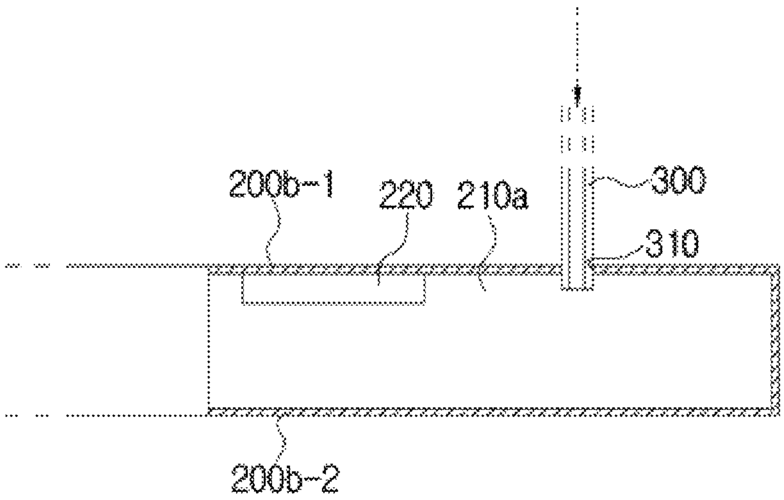
FIG. 3A, FIG. 3B, and FIG. 4 are views illustrating a process of making a space for collecting urine or feces in the diaper according to an embodiment of the invention.
Figure 3B:
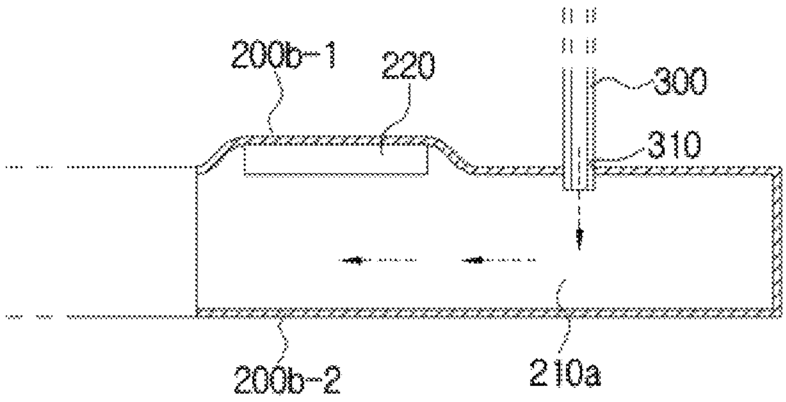
Figure 4:
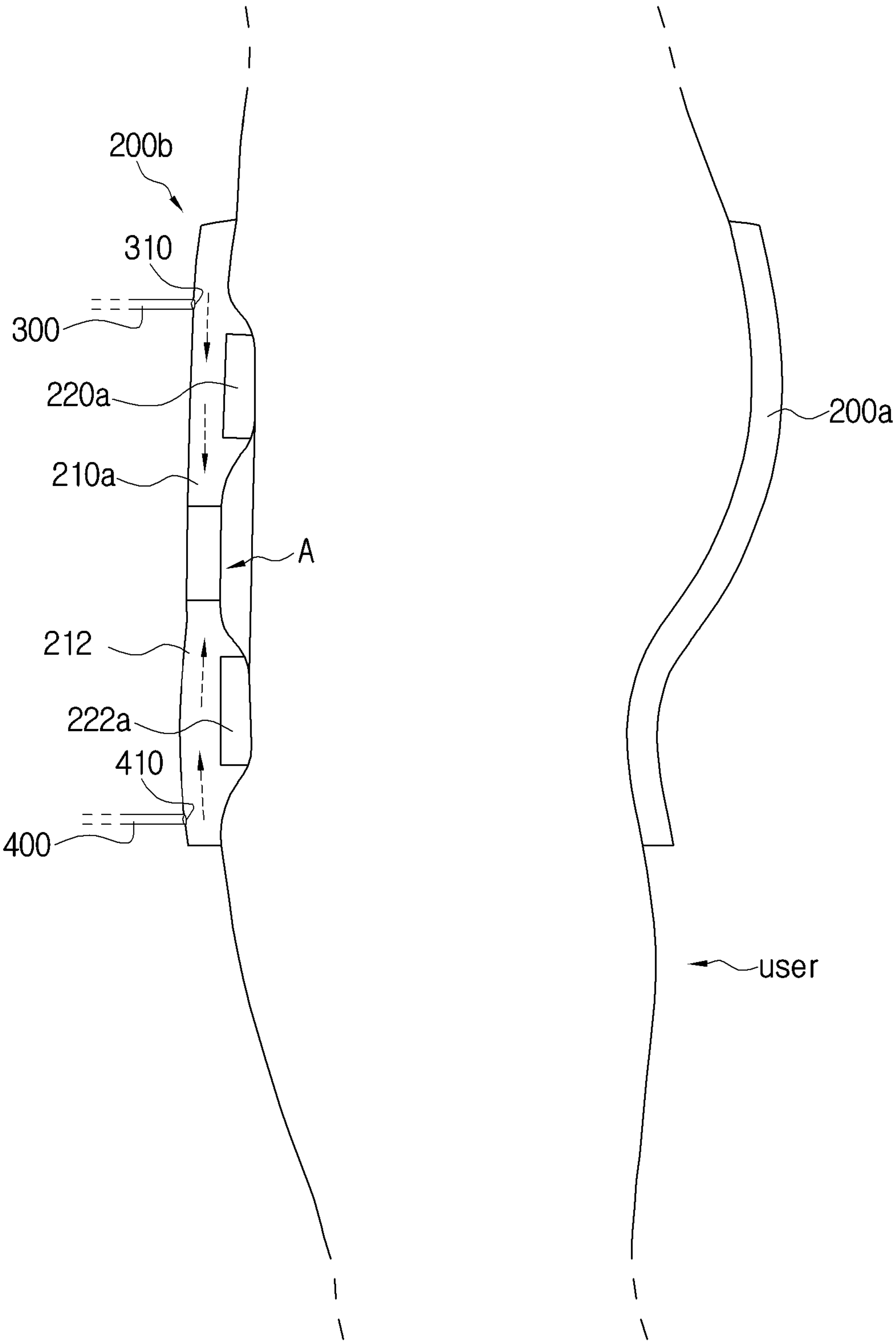
Figure 5A:
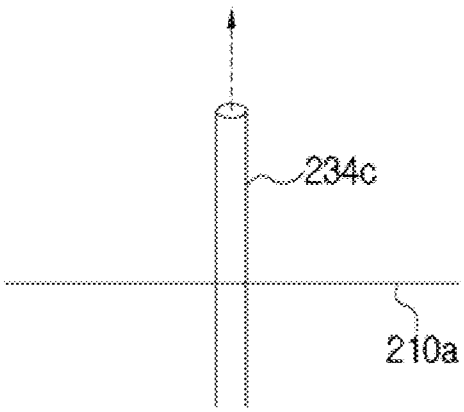
FIG. 5A and FIG. 5B are a view illustrating a cleaning structure according to an embodiment of the invention.
Figure 5B:
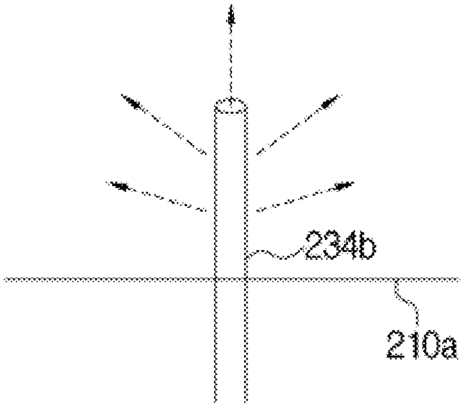

FIG. 1 is a view illustrating patient lying on a bed, and FIG. 2 is a view illustrating a diaper according to an embodiment of the invention. FIG. 3A, FIG. 3B, and FIG. 4 are views illustrating a process of making a space for collecting urine or feces in the diaper according to an embodiment of the invention, and FIG. 5A and FIG. 5B are a view illustrating a cleaning structure according to an embodiment of the invention.

The diaper of the present embodiment is for example pants which patient lying on a bed puts on, and it may dispose of urine/feces several times. Here, the diaper may be used without limitation of usage age, sex etc., and it may be referred to as pants for urine/feces in view of disposing of urine/feces. That is, the diaper is not limited as a diaper for old man, patient or baby and involves every pants capable of disposing of urine/feces.

In FIG. 2, the diaper of the present embodiment includes a front side 200*a*, a back side 200*b* and a connection side 200*c* (bottom part) for connecting the front side 200*a* to the back side 200*b*.

The diaper may be worn like a trouser, or is attached type like the diaper for baby. For example, open and close type Velcro or a zipper (locking device) may be formed on left or right of the front side 200*a*, which is not shown in FIG. 2.

Of course, the locking device may be formed on the back side 200*b*. However, it is efficient that the locking device is formed on the front side 200*a* because many elements are formed on the back side 200*b* as described below.

The back side 200*b* includes a hip section 210, a first thigh section 212 and a second thigh section 214. Here, the hip section 210 may have hip supports 220*a* and 220*b* for supporting left hip and right hip.

The hip supports 220*a* and 220*b* support left or right hip and lift the hip while the user relieves himself (urinates or evacuates), and they are for example pads.

In an embodiment, the hip supports 220*a* and 220*b* may have the structure shown in FIG. 3A and FIG. 3B. Particularly, the hip support 220 may be formed on an internal surface 200*b*-1 of the back side 200*b* in a space between the internal surface 200*b*-1 and an outer surface 200*b*-2 of the back side 200*b*. Here, the internal surface 200*b*-1 may mean a part contacted with the hip of patient, and the outer surface 200*b*-2 may indicate a part touched with a bed.

An air injection pipe 300 may be combined with the internal surface 200*b*-1 or the outer surface 200*b*-2 through a connection section 310.

The hip support 220 is lifted as shown in FIG. 3B when an air injection section (not shown) injects air into the space 210*a* between the internal surface 200*b*-1 and the outer surface 200*b*-2 through the air injection pipe 300 as shown in FIG. 3A. As a result, left hip and right hip are lifted by the hip supports 220*a* and 220*b*, and so a space A having shape of a bowl may be formed by the hip section 210 and the connection side 200*c* as shown in FIG. 4. The space A for collecting urine or feces may be formed by the hip section 210, the connection side 200*c* and thigh sections 212 and 214 corresponding to a thigh support 222 as shown in FIG. 4, when thigh is lifted by the thigh support 222 as follows.

The space A is a space for collecting urine or feces, and urine or feces in the space A is not nearly contacted with a skin of patient because the hip is lifted by the hip supports 220*a* and 220*b*. That is, contact of the skin of patient and the feces may be minimized, and so it is hygienic.

In above description, the space A is formed by injecting the air into the space 210*a* between the internal surface 200*b*-1 and the outer surface 200*b*-2. However, methods of forming the space A may be variously modified as long as the space A is formed by lifting the left hip and the right hip. For example, the hip supports 220*a* and 220*b* may be lifted by using a mechanical driving.

In an embodiment, a first thigh support 222*a* may be formed on the first thigh section 212, and a second thigh support 222*b* may be formed on the second thigh section 214.

The thigh support 222*a* or 222*b* may be formed on an internal surface of the thigh section 212 or 214 in a space between the internal surface and an outer surface of the thigh section 212 or 214 as shown in FIG. 4, and it may be lifted by an air injected through an air injection pipe 400 and a connection section 410. As a result, left thigh or right thigh may be also lifted by the thigh supports 222*a* and 222*b*.

In this case, the space A having shape of bowl may be formed well as shown in FIG. 4. Furthermore, urine or feces and contaminated water due to cleaning may not be leaked outside because the thigh sections 212 and 214 of the back side 200*b* are closed to the thigh of patient. As a result, the bed or patient may not get dirty.

In an embodiment, a waist support 224 may be further formed at vicinity of a waist on the back side 200*b*.

The waist support 224 may also formed on an internal surface of the back side 200*b* and be lifted by an air injected through an air injection pipe (not shown). As a result, the waist support 224 closes to the waist of patient, and thus urine or feces and contaminated water may not be leaked outside.

A discharge pipe 230, at least one cleaning pipe 234 and a dry pipe 240 may be formed on the back side 200*b*.

One terminal of the discharge pipe 230 may be connected to a collection section 250, the other terminal of the discharge pipe 230 may be connected to the back side 200*b* through a connection section 232, and the discharge pipe 230 may inhale urine or feces and the contaminated water. Here, the discharge pipe 230 is removable from the back side 200*b* through the connection section 232.

In an embodiment, the discharge pipe 230 may correspond to the space A for collecting urine or feces. Accordingly, urine or feces and the contaminated water in the space A may be collected to the collection section 250 through the discharge pipe 230.

In an embodiment, a urine sensor may exist in the discharge pipe 230, and thus collected urine may be automatically shifted to the collection section 250 when the urine sensor senses the urine. For example, the collection section 250 may collect the urine by inhaling automatically the urine when the urine sensor senses the urine.

In an embodiment, a weight sensor, etc. may locate below the collection section 250, and a controller may make automatically the collection section 250 empty or notify a manager when the urine/feces or contaminated water is more than a preset level in the collection section 250.

On the other hand, the diaper of patient is exchanged while the patient lies on, and thus a hole may be formed on a part of the bed, and the discharge pipe 230 may be connected to the collection section 250 through the hole of the bed. Of course, the discharge pipe 230 may be extended outside on a top side of the bed without forming the hole on the bed.

The collection section 250 is not limited as long as it collects urine or feces and the contaminated water through inhalation of urine or feces and the contaminated water, and it may include an inhalation means (not shown).

One terminal of the cleaning pipe 234 may be connected to a wash water section 238, the other terminal of the cleaning pipe 234 may be connected to the back side 200*b* through corresponding connection section 236 or 242, and the cleaning pipe 234 is removable.

In an embodiment, the cleaning pipe 234 may be formed outside the space A of the back side 200*b*. This is because the cleaning pipe 234 should not be blocked by urine or feces. However, since the cleaning pipe 234 should be used for cleaning bowel, it may be disposed toward an anus.

For example, the cleaning pipe 234 may be disposed toward the anus in a left direction or a right direction of the anus, and it may swing depending on spurt water pressure.

In an embodiment, the cleaning pipe 234 may have a structure for emitting straightly wash water as shown in FIG. 5A or have plural emitting holes so that the wash water spreads out as shown in FIG. 5B. Here, the cleaning pipe 234 may be flat on the back side 200*b* or be projected from the back side 200*b* as shown in FIG. 5A and FIG. 5B.

However, the cleaning pipe 234 may be normally flat on the back side 200*b* and be projected from the back side 200*b* while the user relieves himself.

The wash water section 238 may be a tank for storing the wash water and may function as a pump to output the wash water through the cleaning pipe 234. For another example, the wash water section 238 may be directly connected to a water pipe, and the cleaning pipe 234 may be removable from the wash water section 238.

In an embodiment, capacity of wash water included in the wash water section 238 may be automatically detected, and wash water may be automatically supplied to the wash water section 238 when capacity of the wash water section 238 becomes smaller than a predetermined level. For example, the weight sensor located below the wash water section 238 may measure the weight of the wash water section 238, and the controller (not shown) may detect current capacity of the wash water section 238 through the measured result and thus supply wash water to the wash water section 238 when the capacity of the wash water is less than the predetermined level. As a result, the wash water section 238 may always secure sufficiently the wash water.

One terminal of the dry pipe 240 may be connected to a dry section (not shown), the other terminal of the dry pipe 240 is connected to the back side 200*b* through the connection section 242, and the dry pipe 240 may be removable from the back side 200*b*.

The dry section may dry a hip cleaned by the wash water by outputting wind through the dry pipe 240.

On the other hand, the dry operation may output a moderate wind to a user's skin, e.g. a skin of patient in ordinary day at which the urine/feces is not discharged as well as when the urine/feces is discharged. Skin disease such as a bedsore may occur because the patient spends usually in bed. Accordingly, the controller may output continuously the moderate wind to the skin of patient to prevent the skin disease. Here, intensity of wind in ordinary day may be smaller than that of wind used for drying the skin after the urine is discharged.

In another embodiment, a box including a urine/feces discharging device (for example vacuum pump) may exist and a fan may be established to the box. In this case, the urine/feces discharging device may be connected to the discharge pipe, inhale the urine/feces when the urine/feces is discharged so that the urine/feces is collected to the collection section. The fan may rotate continuously even when the urine/feces is not discharged, and thus air in the pants for urine/feces is inhaled through the discharge pipe when the fan rotates, thereby emitting the inhaled air outside through the fan of the box. In this case, outer air may be naturally inputted in the pants for urine/feces to prevent the skin disease.

The fan may rotate when the urine/feces is inhaled through the discharge pipe, wherein rotation velocity of the fan when the urine/feces is disposed of is rapider than that of the fan when the urine/feces is not disposed of. The urine/feces inhaled through the discharge pipe may be collected in response to rotation of the fan, and the inhaled air may be emitted outside through the fan. That is, the fan may be slowly rotated and the air in the pants for urine/feces may be emitted outside to prevent the skin disease, in ordinary day at which the urine/feces is not disposed of Whereas, the fan may be rapidly rotated to discharge quickly the urine/feces when the urine/feces is disposed of. On the other hand, the fan may not rotate at night.

In still another embodiment, a temperature sensor may be set to the box or outside the box, and the temperature sensor may measure temperature of air emitted through the discharge pipe. The controller may increase rotation velocity of the fan as the temperature becomes higher. That is, the temperature in the pants for urine/feces is measured, and then the controller may increase the rotation velocity of the fan when the temperature is high and decrease the rotation velocity of the fan when the temperature is low. On the other hand, the rotation velocity of the fan when the temperature is high in ordinary day may be smaller than that of the fan when the urine/feces is disposed of.

In still another embodiment, hole may exist aside the fan of the box, and an open-close section for opening or closing the hole may exist. The open-close section may be closed except when the urine/feces is disposed of. For example, the open-close section may be open when the urine/feces is discharged so that the air inhaled through the discharge pipe is well emitted. For example, the hole may be opened according as fabric is naturally opened by the air if the fabric blocks the hole. Whereas, the open-close section may close the hole when the fan emits outside the air in the pants for urine/feces through the discharge pipe in ordinary day. Air inputted through the hole is emitted outside by the fan if the hole is opened, and thus the hole may be closed to prevent this problem.

Extra dry wind may not be outputted to the user's hip, etc. if the fan is used. That is, the pants for urine/feces using the fan may not use extra dry pipe, etc. This is because the fan performs a dry operation and air circulation for preventing the skin disease.

In still another embodiment, the collection section connected to the discharge pipe of the pants may be connected to the pump (for example a motor for a vacuum cleaner) or the box in which the pump locates through a pipe. As a result, the urine/feces or the contaminated water may be collected to the collection section through the discharge pipe, air in the collection section may be inhaled through the pipe by the pump, and the inhaled air may be emitted outside through the pump or the fan. Of course, the pump may perform an inhaling operation to collect the urine/feces or the contaminated water through the discharge pipe.

Briefly, the diaper of the invention may make the space A for collecting urine or feces by using the hip supports 220*a* and 220*b* and the thigh supports 222*a* and 222*b*, clean the anus by using the wash water while the user relieves himself, collect urine, feces and the contaminated water in accordance with the cleaning in the collection section 250, and dry the hip or the anus wet by the wash water by using the wind.

Accordingly, it is not necessary to exchange the diaper though patient relieves himself several times a day and the user may reuse after washing the diaper though he uses continuously the diaper all day or for days. As a result, it is not necessary to exchange frequently the diaper of patient, and so family member or caregiver may make less an effort and environment pollution may reduce.

On the other hand, related information may be automatically provided to a manager when amount of the urine/feces or the contaminated water is more than a preset value or amount of wash water of the wash water section is less than a predetermined level. For example, a red light may be emitted from a board managed by the manager. A lighting means for the collection section and a lighting means for the wash water may exist independently on the board.

The diaper of the invention may further include an elasticity section 216 for tightening a waist and a sensor (not shown) for sensing urine or feces through moisture and gas generated when the user relieves himself, a light sensor for sensing the urine/feces by using a light or a sensor for sensing the urine/feces through contact with the urine/feces or weight of the urine/feces, which is not described above.

The elasticity section 216 may reduce tightening of patient by the diaper when the diaper is expanded by injection of the air. Another elasticity section may be formed on the thigh section 214 of the diaper.

The sensor may be disposed in an internal space of the diaper or formed on an internal surface of the diaper. That is, location of the sensor is not limited as long as the sensor can sense urine or feces. However, it is efficient that the sensor is formed below the hip. This is for sensing immediately gas, etc. outputted from an anus.

Moreover, multiple embossed projection patterns, a crease, etc. may be formed on an upper part of the diaper, and thus touch of the internal surface of the diaper and a skin of patient may be minimized and the air may be naturally circulated.

Furthermore, a stopper may be adhered to the connection section 236 connected to the cleaning pipe 234. This is for blocking a hole of the connection section 236 when the cleaning pipe 234 is separated from the diaper.

Additionally, a massage function may be added on the upper part (corresponding to the waist) of the diaper. The massage may be provided to the waist if an operation of lifting or downing the hip and the thigh of patient is repeated depending on the injection of the air.

Furthermore, a thermal function may be further embodied to an upper part (corresponding to the waist) of the diaper.

Hereinafter, a process of disposing of urine or feces in the diaper of the invention will be described. It is assumed that the patient lies on the bed.

The diaper is worn to the patient and then the discharge pipe 230, the cleaning pipe 234 and the dry pipe 240 may be connected to the diaper. Of course, the discharge pipe 230, the cleaning pipe 234 and the dry pipe 240 may be connected to the diaper before the diaper is worn.

Subsequently, the sensor senses discharging of the urine/feces by using blocking of the light due to moisture, gas, weight of the urine/feces.

Then, the hip supports 220*a* and 220*b* and the thigh supports 222*a* and 222*b* are lifted depending on the injection of the air when the urine or feces is sensed. As a result, the hip and the thigh of patient rises and the space A having the shape of bowl may be formed by the hip section 210 and the connection side 200*c*. Here, urine or feces is collected in the space A, and so a phenomenon that urine or feces is touched with the skin of the patient is minimized.

On the other hand, the waist support 224 may be lifted together when the hip supports 220*a* and 220*b* and the thigh supports 222*a* and 222*b* are lifted.

Subsequently, the wash water may be outputted to the anus through the cleaning pipe 234 when it is determined that the emission of urine or feces is completed.

Then, a dry wind may be outputted through the dry pipe 240 to dry the anus wet by the wash water, when output of the wash water is completed.

Subsequently, urine or feces and contaminated water by the wash water are collected to the collection section 250 through the discharge pipe 230. This collecting process may be performed before drying or be performed with drying.

The hip supports 220*a* and 220*b*, the thigh supports 222*a* and 222*b* and the waist support 224 are returned to an original position, when the collecting is completed. That is, lifted hip supports 220*a* and 220*b*, lifted thigh supports 222*a* and 222*b* and lifted waist support 224 may be downed.

Subsequently, urine or feces and the contaminated water collected by the collection section 250 may be dumped.

FIG. 6A, FIG. 6B, FIG. 6C, and FIG. 6D are a view illustrating schematically a part of a diaper according to another embodiment of the invention.

Figure 6A:
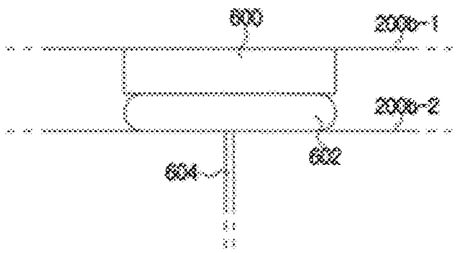
FIG. 6A, FIG. 6B, FIG. 6C, and FIG. 6D are a view illustrating schematically a part of a diaper according to another embodiment of the invention.

Referring to FIG. 6A, a hip support 600 and an expansion section 602 (for example, balloon) may be laminated in a space between an internal surface 200*b*-1 and an outer surface 200*b*-2 of a back side of the diaper. That is, unlike only the hip support exists in the space between the internal surface 200*b*-1 and the outer surface 200*b*-2, in the present embodiment, the hip support 600 and the expansion section 602 may exist in the space between the internal surface 200*b*-1 and the outer surface 200*b*-2.

In another embodiment, the hip support 600 and the expansion section 602 may locate inside the back side of the diaper or be disposed outside the back side. One of the hip support 600 and the expansion section 602 may be disposed inside the back side and the other one may locate outside the back side.

Figure 6C:
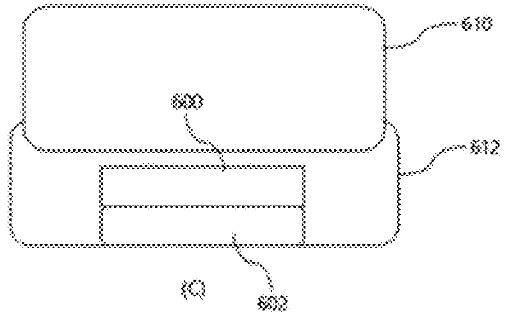
Figure 6B:
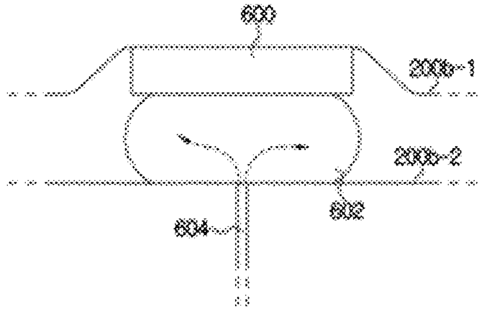

In the event that air is injected to the expansion section 602 through an air injection pipe 604, the expansion section 602 is expanded as shown in FIG. 6B, thereby lifting the hip support 600. As a result, the hip of patient may rise.

In another embodiment, the expansion section 602 may locate on the hip support 600. In this case, the hip of patient may be lifted when the expansion section 602 is expanded.

A thigh support and another expansion section may be laminated in the space between the internal surface 200*b*-1 and the outer surface 200*b*-2 of a back side of the diaper in view of the thigh, which is not shown in FIG. 6A, FIG. 6B, FIG. 6C, and FIG. 6D. The thigh support may be lifted according as air is injected to the expansion section.

In another embodiment, the hip support and the expansion section may locate inside the back side of the diaper or be disposed outside the back side. One of the hip support and the expansion section may be disposed inside the back side and the other one may locate outside the back side.

A space where urine or feces is collected is formed when the hip support 600 and the thigh supports rise. Any further description concerning the space will be omitted because it is described above.

In another embodiment, a diaper (pants) may include a first sub diaper (first sub pants) 610 and a second sub diaper (second sub pants) 612 as shown in FIG. 6C. That is, the second sub diaper 612 having internal space may be connected to an outer surface of the first sub diaper 610 with the structure in FIG. 2. For example, the second sub diaper 612 is fabric, the space may be formed in the second sub diaper 612 according as end parts of the second sub diaper 612 are connected to the outer surface of the first sub diaper 610, and the second sub diaper 612 may corresponds to only a hip. Here, the fabric may be adhered to the first sub diaper 610 by using a Velcro. In other words, the second sub diaper 612 may be removable from the first sub diaper 610.

The hip of patient may locate in the first sub diaper 610, and the hip support 600 and the expansion section 602 may locate in the second sub diaper 612. However, laminating order of the hip support 600 and the expansion section 602 may be freely designed. For example, the expansion section 602 may locate below the hip support 600, but it may be disposed on the hip support 600. In this case, the hip is lifted when the expansion section 602 is expanded, and so a space in which the urine/feces is collected may be formed.

Of course, a thigh support and corresponding expansion section may locate in the second sub diaper 612.

Figure 6D:
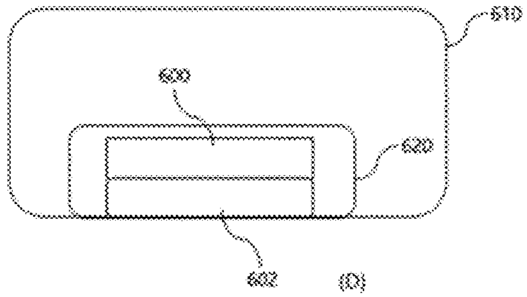

In another embodiment, a third sub diaper (third sub pants) 620 may be formed in the first sub diaper 610, and the hip support 600 and the expansion section 602 may locate in the third sub diaper 620, as shown in FIG. 6D. Of course, the thigh support and corresponding expansion section may locate in the third sub diaper 620.

In still another embodiment, the hip support 600 and the thigh support may locate in the first sub diaper 610 and corresponding expansion sections may be disposed in the second sub diaper 612 or the third sub diaper 620. However, it is effective that the hip support 600 and the expansion section 602 locate together in the second sub diaper 612.

On the other hand, the space where the urine/feces is collected may be formed by using only the expansion sections without using the hip support and the thigh support. however, the urine of patient may flow outside the pants for urine/feces when air is not injected to the expansion sections if only expansion sections exist. Whereas, a basic space may be formed by the hip support and the thigh supports though air is not injected to the expansion sections, if the hip support and the thigh supports exist together with the expansion sections. As a result, the urine of patient may not flow outside the pants for urine/feces though the air is not injected to the expansion sections. Accordingly, it is efficient that the hip support, the thigh support and the expansion sections exist together.

Additionally, the skin may be separated from a bottom surface of the diaper because the supports have certain height, thereby preventing skin disease such as bedsore, etc.

In still another embodiment, a space division member may be formed in the diaper, and thus the diaper may include two spaces. The user's hip, etc. may be inserted into an upper space of the spaces, and the support and the expansion section may locate in a lower space of the spaces. Here, the space division member may be removable from the diaper.

Figure 7:
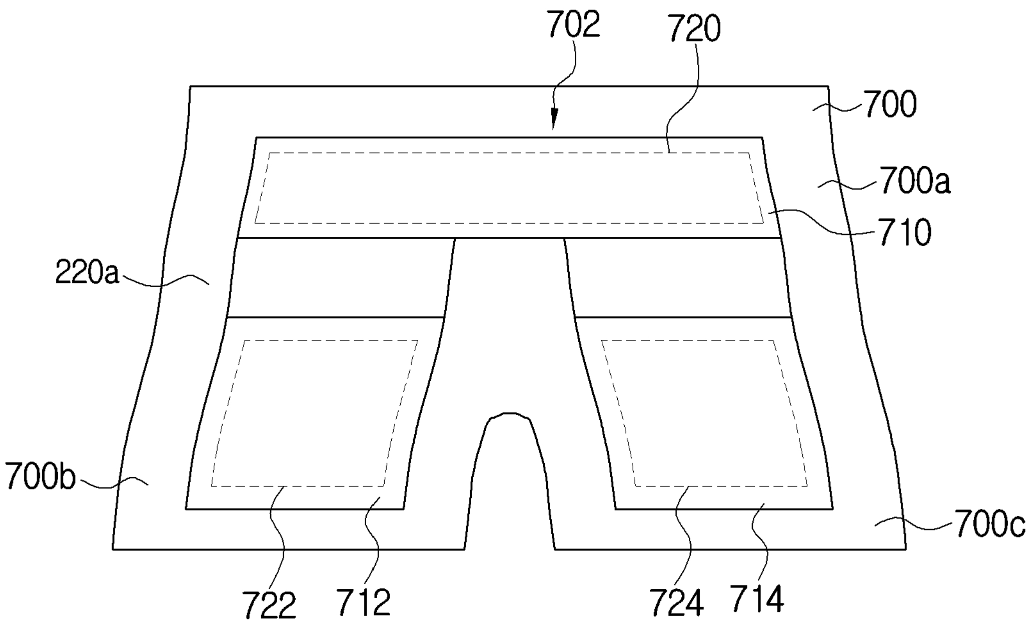
FIG. 7 is a view illustrating schematically a part of a diaper according to still another embodiment of the invention.
Figure 8:
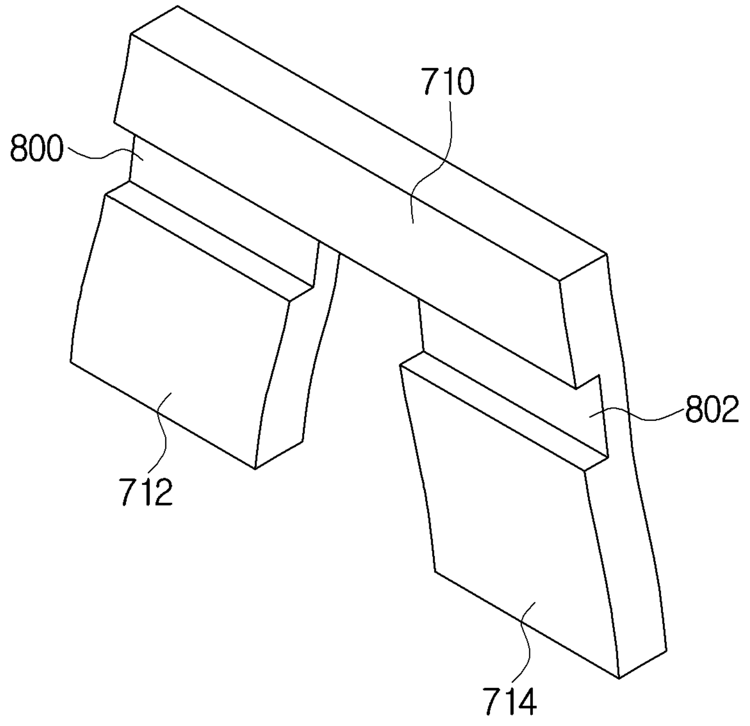
FIG. 8 is a view illustrating a supporting member according to an embodiment of the invention.
Figure 9A:
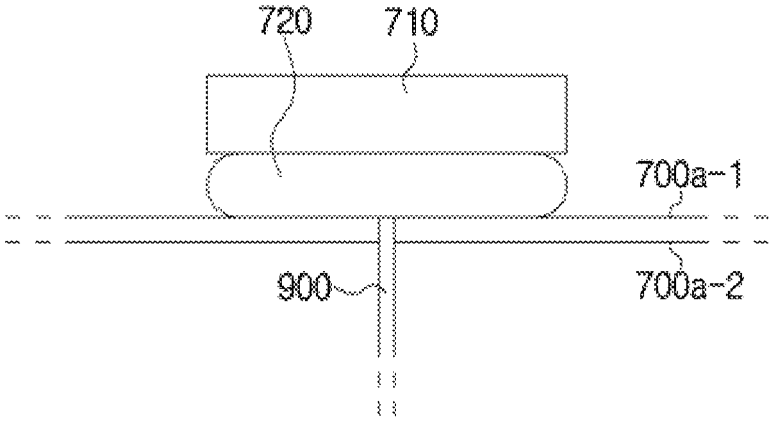
FIG. 9A and FIG. 9B are a view illustrating an operation of a hip support according to an embodiment of the invention.
Figure 9B:
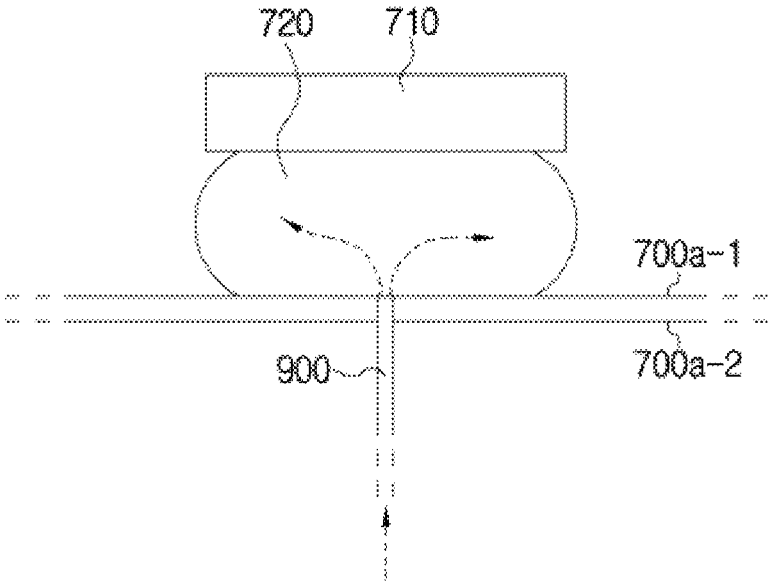
Figure 10A:
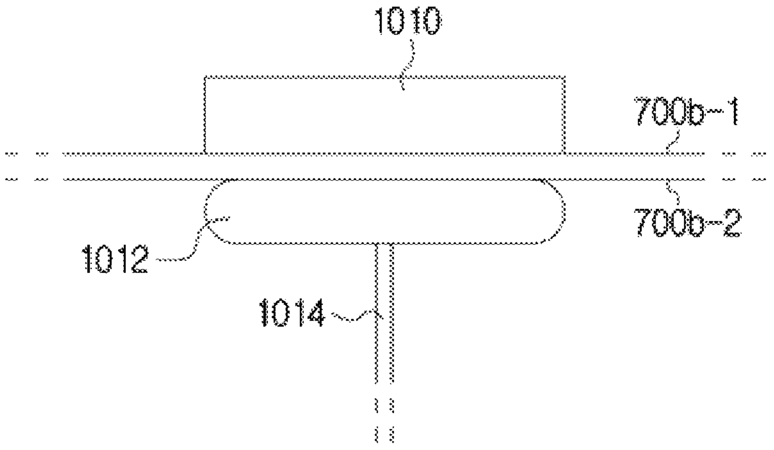
FIG. 10A and FIG. 10B are a view illustrating an operation of a thigh support according to an embodiment of the invention.
Figure 10B:
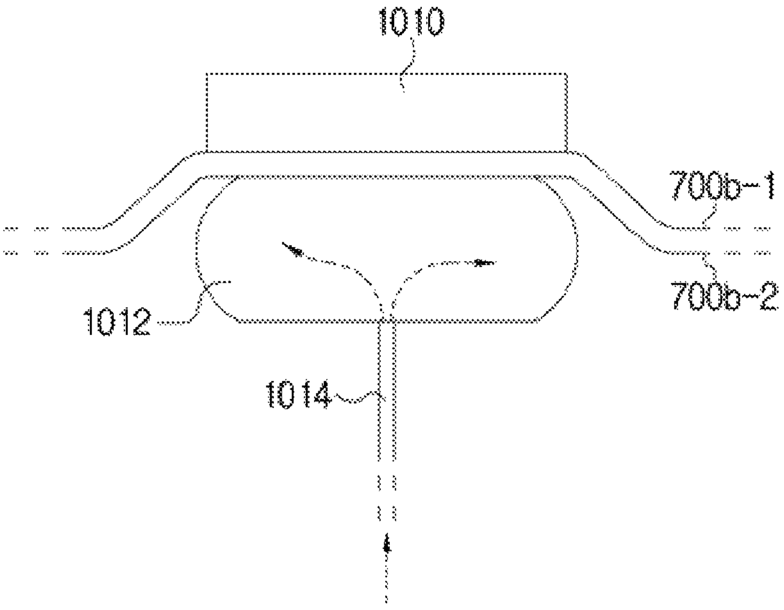
Figure 11:
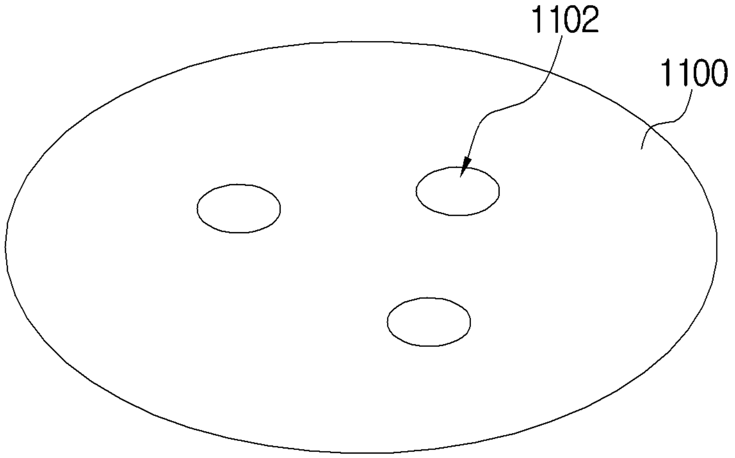
FIG. 11 is a view illustrating a pipe structure according to an embodiment of the invention.

FIG. 7 is a view illustrating schematically a part of a diaper according to still another embodiment of the invention, and FIG. 8 is a view illustrating a supporting member according to an embodiment of the invention. FIG. 9A and FIG. 9B are a view illustrating an operation of a hip support according to an embodiment of the invention, and FIG. 10A and FIG. 10B are a view illustrating an operation of a thigh support according to an embodiment of the invention. FIG. 11 is a view illustrating a pipe structure according to an embodiment of the invention. However, FIG. 7 shows only the back side of the diaper, for the purpose of convenience of description.

In FIG. 7, the supporting member 702 may locate on a hip section 700*a* of an internal surface of a back side 700 of the diaper, and expansion section 720, 722 and 724 may be disposed between the internal surface and the supporting member 702. In another embodiment, the expansion section 722 and 724 may locate below an outer surface of the back side 700 of the diaper.

The supporting member 702 may include a hip support 710, a first thigh support 712, a second thigh support 714, a connection section 800 for connecting the hip support 710 to the first thigh support 712 and a second connection section 802 for connecting the hip support 710 to the second thigh support 714. That is, the hip support 710 and the thigh supports 712 and 714 have integral structure. Of course, the hip support 710 and the thigh supports 712 and 714 may be independent members and the connection sections 800 and 802 don't exist.

In an embodiment, the hip support 710 and the thigh supports 712 and 714 may have height greater than the connection section 800 or 802, and a cleaning pipe, etc. may be crossly disposed over the connection sections 800 and 802.

Referring to FIG. 9A and FIG. 9B, an expansion section 720 located between the hip support 710 and an internal surface 700*a*-1 of the hip section 700*a* expands when air is injected to the expansion section 720. As a result, the hip support 710 is lifted, and thus the hip rises.

In FIG. 10A and FIG. 10B, the thigh support 1010 is disposed on an internal surface 700*b*-1 of a thigh section of the back side 700 of the diaper, and an expansion section 1012 is disposed below an outer surface 700*b*-2 of the thigh section. In the event that air is injected into the expansion section 1012 through an air injection pipe 1014, the thigh support 1010 is lifted, and thus the thigh rises.

Of course, the expansion section and the thigh support 1010 may be sequentially disposed on the internal surface 700*b*-1. On the other hand, since the thigh section rises in FIG. 10, it is efficient to move urine, etc. in the direction of a discharge pipe.

Briefly, a space for collecting urine or feces may be naturally formed according as the hip support 710 and the thigh supports 1010 rise.

The discharge pipe, a cleaning pipe and a dry pipe are not mentioned in above embodiments, they are the same as in FIG. 1 to FIG. 6D or similar to those in FIG. 1 to FIG. 6D, and thus any further description concerning the same or similar elements will be omitted.

The discharge pipe, the cleaning pipe and the dry pipe may be directly combined with the diaper like above embodiments, or they may be combined with a pipe structure 1100 formed on an internal surface of the diaper as shown in FIG. 11.

For example, the pipe structure 1100 may be formed of hard plastic, and it may include at least one hole 1102 through which the discharge pipe, the cleaning pipe or the dry pipe is combined. That is, the discharge pipe, the cleaning pipe or the dry pipe may be combined with the pipe structure 1100 without being directly combined with the diaper.

Of course, the pipe structure 1100 may have a structure for connecting an outer pipe extended toward the diaper to an inner pipe located inside the diaper.

That is, combination structure and combination method may be variously modified as long as the pipe structure 1100 combines the discharge pipe, the cleaning pipe or the dry pipe.

In another embodiment, the support and at least one expansion section on or below the support may locate in the second sub diaper 612 or the third sub diaper 620 of the diaper as shown in FIG. 6C and FIG. 6D, wherein the diaper includes the first sub diaper 610 and the second sub diaper 612 or the third diaper 620. Of course, the support or the expansion section may locate in the first sub diaper 610 and the expansion section or the support may be disposed in the second sub diaper 612.

Figure 12:
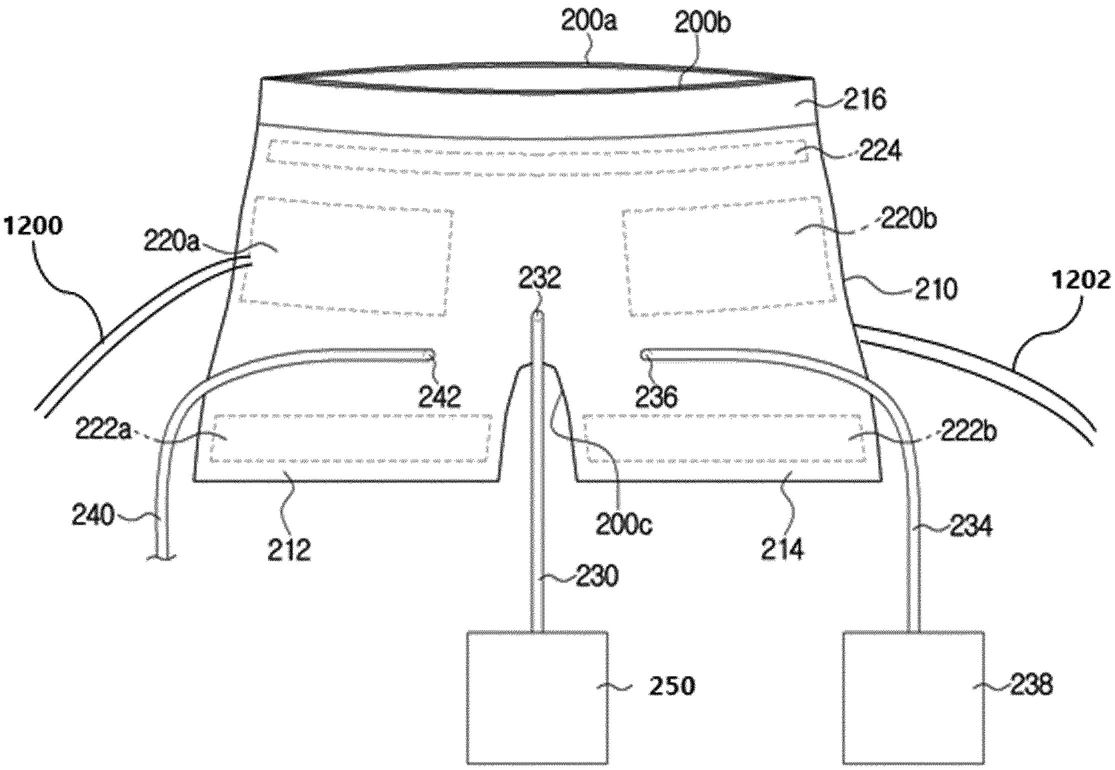
FIG. 12 is a view illustrating schematically a diaper according to still another embodiment of the disclosure.
Figure 13A:
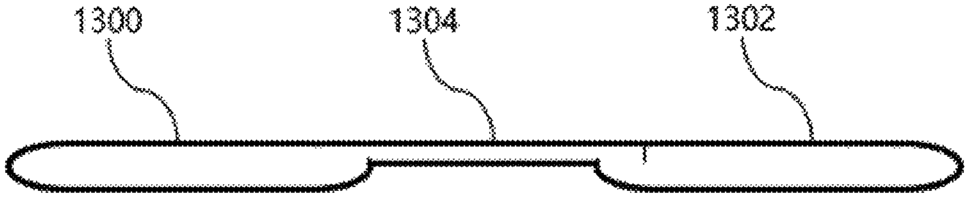
FIG. 13A and FIG. 13B are a view illustrating an expansion section and an emission of urine or feces according to an embodiment of the disclosure.
Figure 13B:
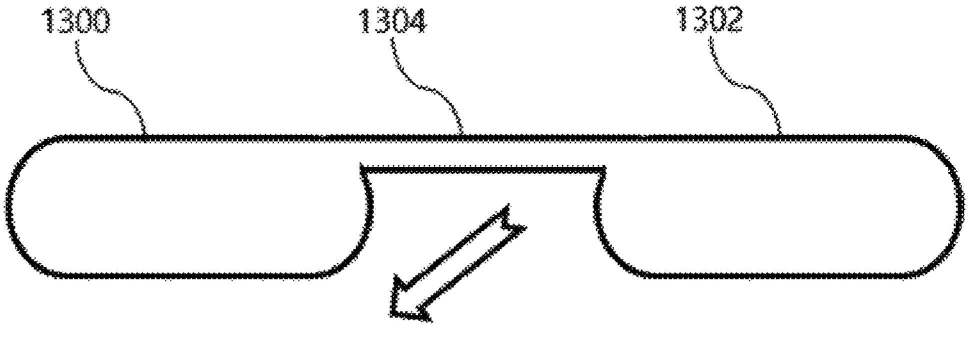
Figure 14:
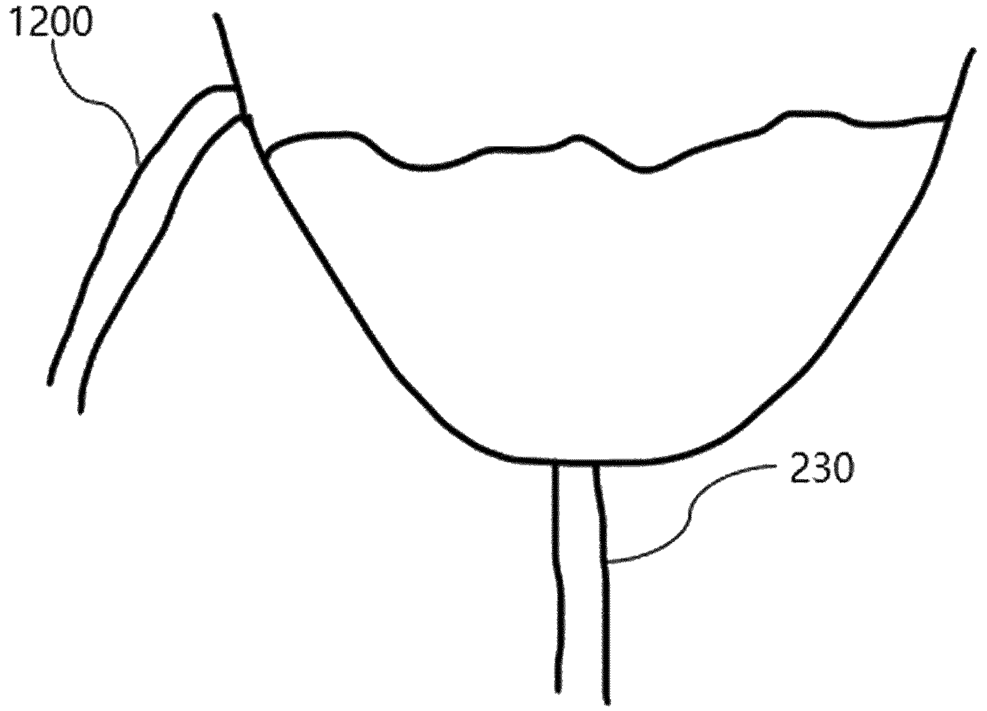
FIG. 14 is a view illustrating an emission of urine or feces according to another embodiment of the disclosure.
Figure 15:
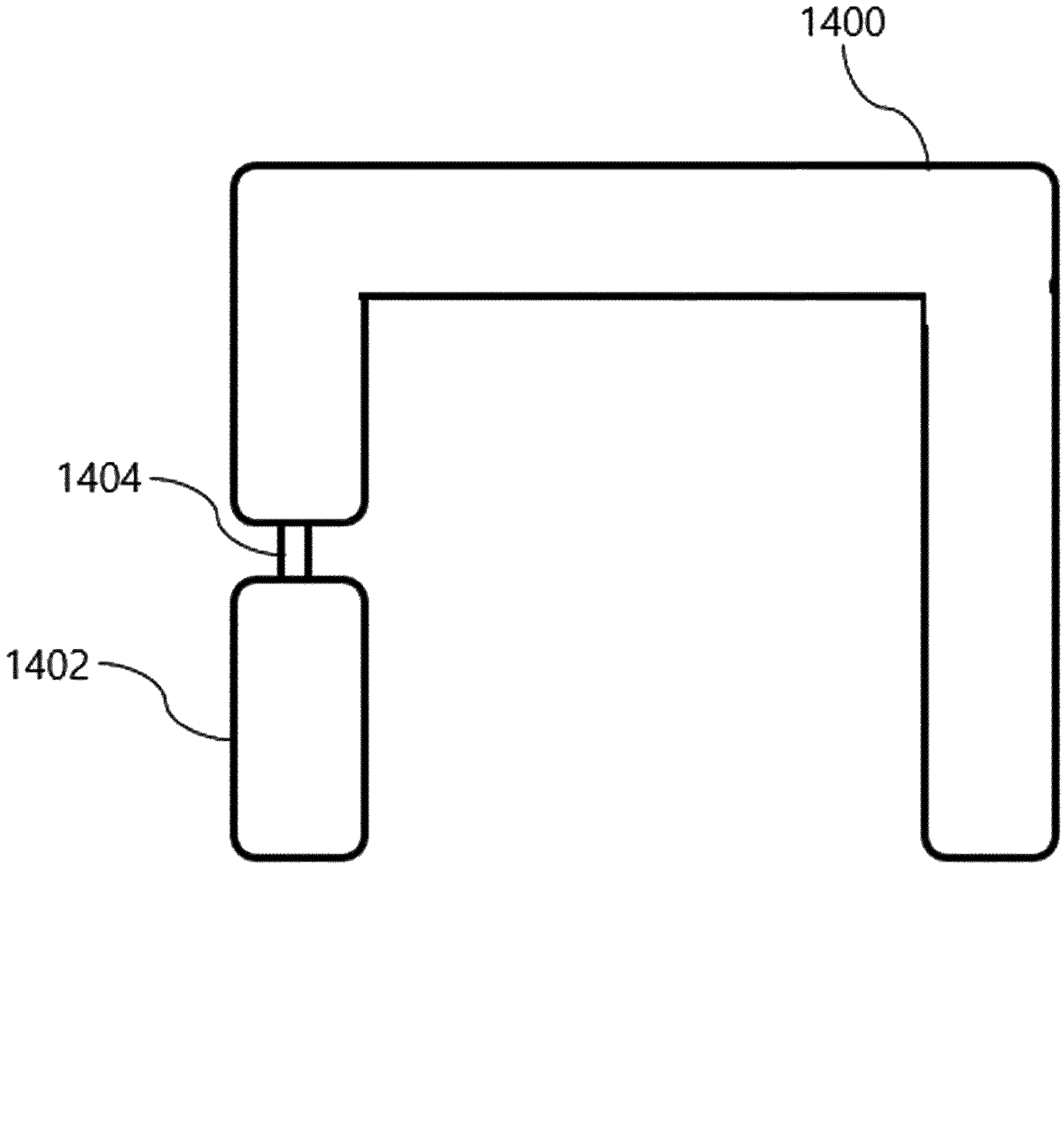
FIG. 15 is a view illustrating an expansion section according to another embodiment of the disclosure.

FIG. 12 is a view illustrating schematically a diaper according to still another embodiment of the disclosure, and FIG. 13A and FIG. 13B are a view illustrating an expansion section and an emission of urine or feces according to an embodiment of the disclosure. FIG. 14 is a view illustrating an emission of urine or feces according to another embodiment of the disclosure, and FIG. 15 is a view illustrating an expansion section according to another embodiment of the disclosure. Here, the same numerical numbers will be used about the same elements as in FIG. 2 to FIG. 11, and any further description about the same elements will be omitted.

In FIG. 12, a second discharge pipe 1200 and a wind shooting section 1202 as well as the first discharge pipe 230 shown in FIG. 2 may further exist to pants (diaper).

The first discharge pipe 230 is connected to a central part of a back side of the diaper, and the second discharge pipe 1200 may be connected to an external member in a direction of the expansion section for lifting a hip support or a thigh support.

Particularly, the expansion section for lifting the hip support or the thigh support may include a first expansion section 1300, a second expansion section 1302 and a connection section 1304 as shown in FIG. 13A and FIG. 13B.

The expansion sections 1300 and 1302 may not be expanded as shown in FIG. 13A before air is injected, and they may be expanded as shown in FIG. 13B when air is injected.

In an embodiment, the connection section 1304 may have a width smaller than the expansion section 1300 or 1302 and be connected to an upper part of the expansion sections 1300 and 1302. As a result, a discharge path is generated under the connection section 1304 when the expansion sections 1300 and 1302 are expanded. Accordingly, urine/feces or contaminated water collected in the space may be discharged through the first discharge pipe 230 and it may be also discharged through the discharge path under the connection section 1304 and the second discharge pipe 1200 as shown in FIG. 14.

In another embodiment, a discharge path may be formed under a part of a support when an expansion section locates on the support.

The air is injected into one of the expansion sections 1300 and 1302 which is not shown, and the injected air may be delivered to another expansion section through the connection section 1304. As a result, the expansion sections 1300 and 1302 may be expanded when the air is injected into one of the expansion sections 1300 and 1302. Of course, the air may be injected to both of the expansion sections 1300 and 1302.

It is difficult to discharge much urine or contaminated water when much feces or contaminated water occurs in FIG. 2. Accordingly, another discharge path is formed under the connection section 1304 of the expansion sections 1300 and 1302 to discharge smoothly the feces or the contaminated water.

The discharge path is formed through only the expansion section for lifting one of the hip support or the thigh supports in the above description, but a discharge path may be formed through the hip support and the thigh supports.

In another embodiment, an expansion section may have a shape of "⊏" as shown in FIG. 15 to lift the hip support and the thigh supports. In this case, a connection section 1404 connects a first expansion section 1400 to a second expansion section 1402 and it may be connected to an upper part of the expansion sections 1400 and 1402. As a result, a discharge path may be formed under the connection section 1404. Here, the first expansion section 1400 may lift a hip and a part of thighs, and the second expansion section 1402 may lift the other part of the thighs.

In another embodiment, the pants may further include a wind shooting section 1202 for shooting out wind so that urine/feces or contaminated water is well-discharged through a discharge path under the connection section. That is, the wind shooting section 1202 may shoot out the wind in a direction of the discharge path so that the feces or the contaminated water flows through the discharge path under the connection section.

Since an old man patient, etc. relieves himself several times a day, much wash water should be outputted in the pants in FIG. 2. As a result, a great quantity of contaminated water occurs, and thus it is necessary to operate several times multiple pumps. A number of patients exist generally in a hospital room. In this condition, operation of multiple pumps causes considerable noise, thereby bringing about inconvenience of other patient. Accordingly, a number or a time of operating the pump for emission of the wash water or urine/feces reduces when it assists to output feces or the contaminated water by using the wind which generates small noise, thereby reducing the noise.

On the other hand, the direction of the dry pipe 240 may be changed to output the wind in a direction of the discharge path after drying the hip, etc. through the dry pipe 240, without using the wind shooting section 1202.

In still another embodiment, a protection member such as vinyl, etc. may locate in the discharge path under the connection section. It is for minimizing contamination, dirt or smell due to output of urine/feces or the contaminated water.

Figure 16A:
FIG. 16A, FIG. 16B, and FIG. 17 are views illustrating a diaper according to still another embodiment of the disclosure.
Figure 16B:
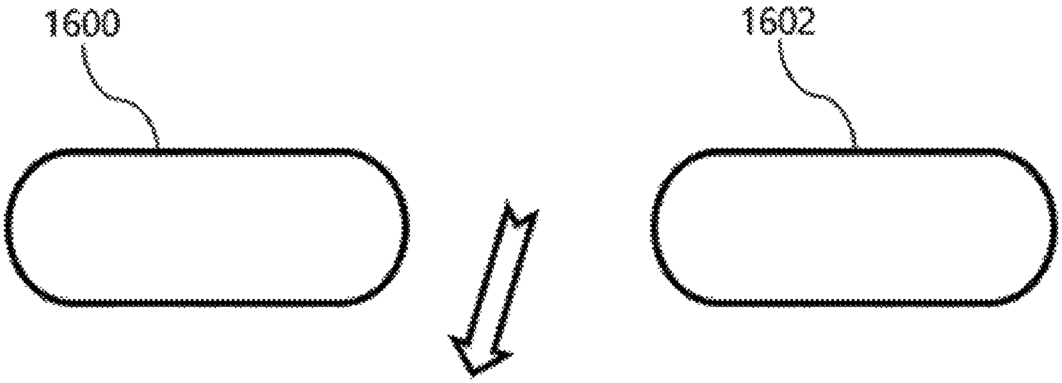
Figure 17:
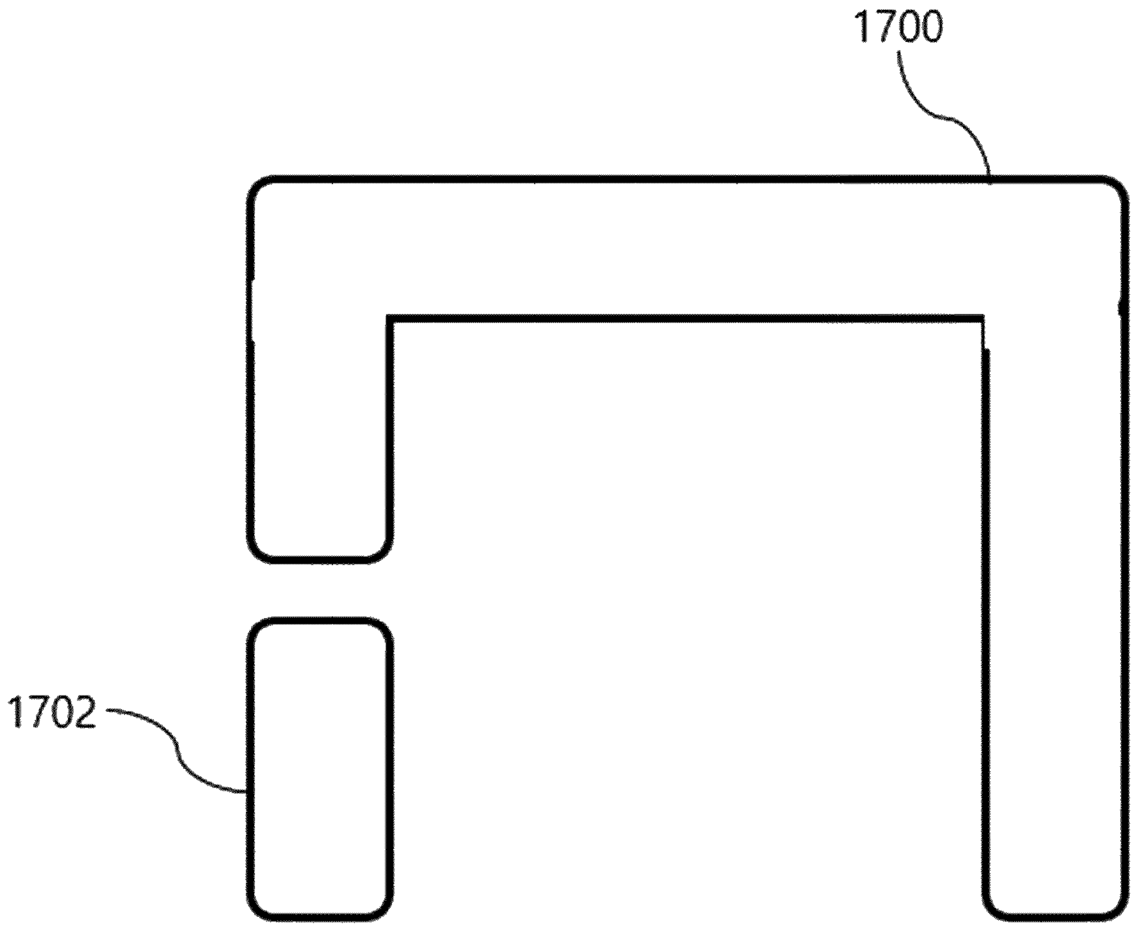

FIG. 16A, FIG. 16B, and FIG. 17 are views illustrating a diaper according to still another embodiment of the disclosure.

In FIG. 16A and FIG. 16B, expansion sections 1600 and 1602 may be separated without using a connection section between the expansion section 1600 and 1602. In this case, a discharge path may be naturally formed when the expansion sections 1600 and 1602 are expanded, and the discharge path may be connected to a discharge pipe. As a result, urine/feces or the contaminated water may be outputted outside through the discharge path and the discharge pipe.

In FIG. 17, expansion sections 1700 and 1702 may have a shape of "⊏" and be separated without using the connection section between the expansion sections 1700 and 1702. As a result, a discharge path may be naturally formed between the expansion sections 1700 and 1702 when the expansion sections 1700 and 1702 are expanded.

Figure 18:
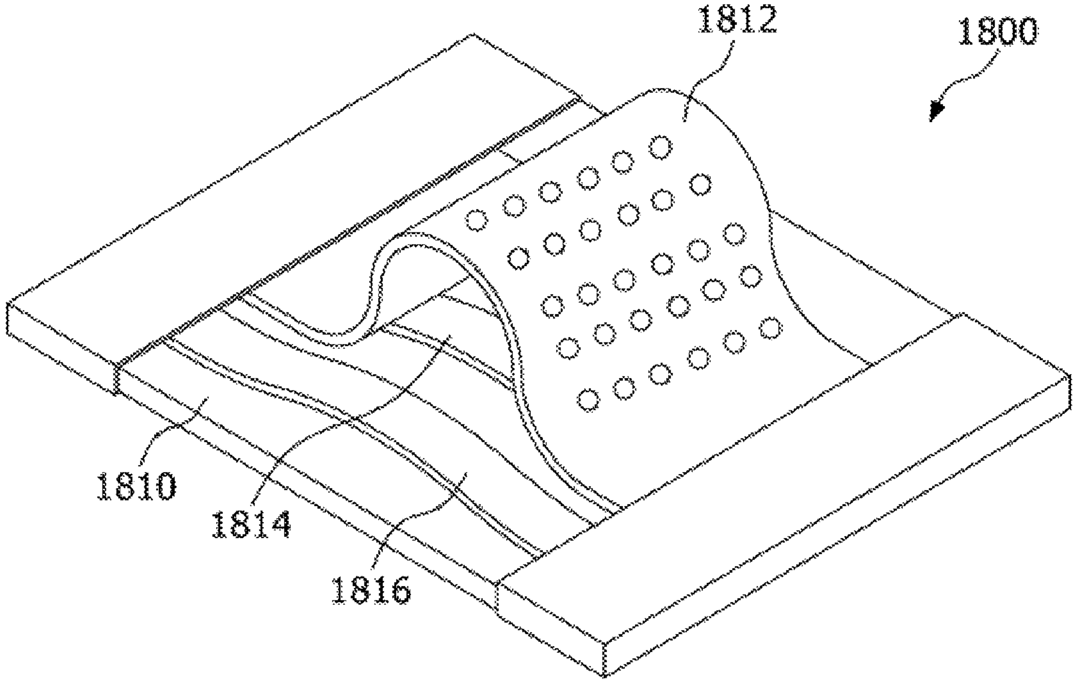
FIG. 18 is a view illustrating a sensor according to an embodiment of the disclosure.

FIG. 18 is a view illustrating a sensor according to an embodiment of the disclosure.

A sensor 1800 may sense urine/feces and locate inside a back side of a diaper. However, the location of the sensor 1800 is not limited as long as the sensor 1800 senses the urine/feces. On the other hand, the sensor may locate in a first sub diaper when the diaper includes the first sub diaper and a second sub diaper.

In an embodiment, the sensor 1800 may include a base section 1810, a cover 1812, a first electrode 1814 and a second electrode 1816 as shown in FIG. 18. A wire for connecting the electrodes 1814 and 1816 to a power supply (not shown) may exist, which is not shown.

The first electrode 1814 is formed on the base section 1810 and is covered by the cover 1812. That is, the cover 1812 covers the first electrode 1814 with located on the first electrode 1814.

The second electrode 1815 may be formed on the base section 1810 and locate outside the cover 1812. That is, the first electrode 1814 is covered by the cover 1812, and the second electrode 1816 is not covered by the cover 1812.

This sensor 1800 may locate inside for example the back side and discriminate through sensing of resistance change whether or not the patient discharges the urine/feces. A washing operation may be performed when it is discriminated that the urine/feces is discharged.

The cover 1812 may be convexly formed over the first electrode 1814 and holes may be formed on the cover 1812. A man's ball or a woman's genital may contact with the electrodes 1814 and 1816 if the cover 1812 is not used. In this case, the electrodes 1814 and 1816 may be electrically connected due to water of the ball or the genital, thereby generating malfunction of the electrodes 1814 and 1816. That is, the sensor 1800 may mis-sense that the urine/feces is discharged though the urine/feces is not discharged.

To solve the problem, the cover 812 is formed on the first electrode 1814 so that the ball or the genital is not directly contacted with the first electrode 1814. On the other hand, the holes passing the urine, etc. may be formed on the cover 1812 because the urine should flow on the first electrode 1814 when the urine/feces is outputted. As a result, the electrodes 1814 and 1816 may be electrically connected because the urine flows on the first electrode 1814 through the holes when the urine/feces is discharged, thereby sensing the urine/feces. A location on which the feces is stacked is shifted backward by a length of the cover 1812 when the cover 1812 is formed. Accordingly, the feces may be stably stacked on a floor board described below.

In another embodiment, the hole may not be formed on the cover 812. For example, the cover 182 may be formed of leather and so on. The electrodes 1814 and 1816 may be connected according as the urine flows on the cover 812 though the hole is not formed on the cover 182.

Of course, the structure of the sensor 1800 is not limited to a structure in FIG. 18 as long as the sensor 1800 can sense the urine/feces.

Figure 19:
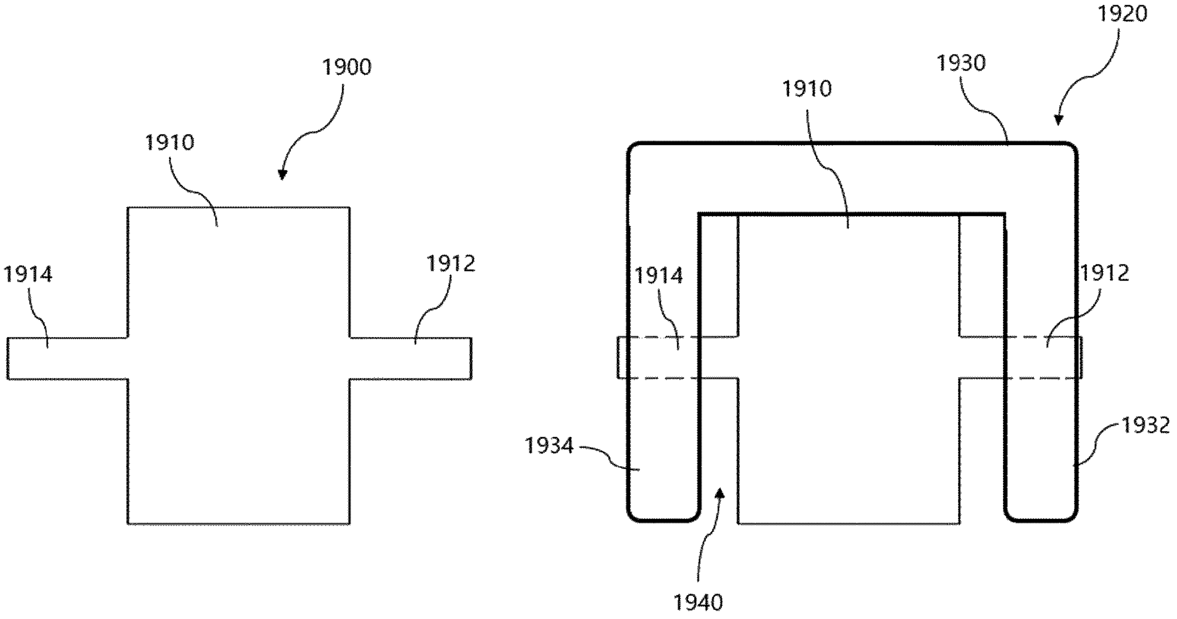
FIG. 19 is a view illustrating a structure and an array of a floor board according to an embodiment of the disclosure.
Figure 20:
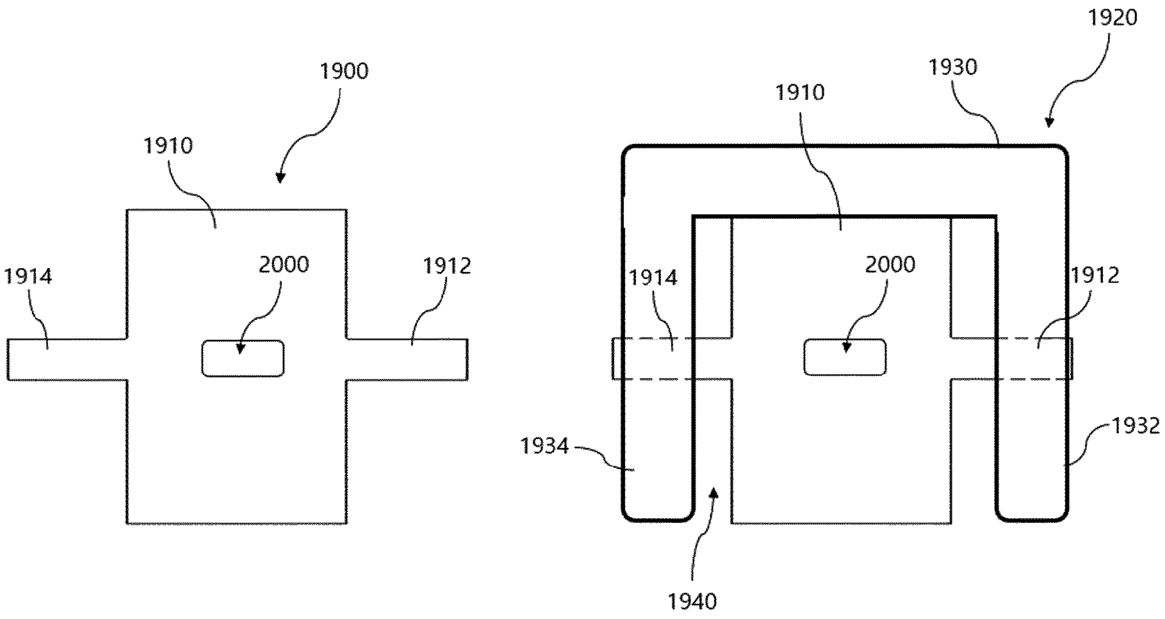
FIG. 20 is a view illustrating a structure and an array of a floor board according to another embodiment of the disclosure.

FIG. 19 is a view illustrating a structure and an array of a floor board according to an embodiment of the disclosure, and FIG. 20 is a view illustrating a structure and an array of a floor board according to another embodiment of the disclosure.

A floor board (output assisting member or assist board) 1900 may locate near for example a groin on an internal surface of a back side of a diaper or an internal surface of a first sub diaper 610, a second sub diaper 612 or a third sub diaper 620. Of course, the floor board 1900 may locate outside the diaper.

An upper surface and a lower surface of the floor board 1900 may be flat. As a result, the feces may be stably stacked and the urine/feces collected in the space may be smoothly slipped in a direction of a discharge section when the floor board 1900 locates on for example the internal surface of the back side of the diaper. That is, the floor board 1900 may assist to shift the urine/feces in the direction of the discharge section.

Additionally, the floor board 1900 may keep stably the space, where the urine/feces is collected, formed by the hip support, thigh supports and expansion sections. A blanket exists generally between the patient and a bed when the patient is lay. In this case, a part of the diaper, specifically a part corresponding to the space may be convexly formed by the blanket, and thus the space where the urine/feces is collected becomes smaller.

However, the part of the diaper corresponding to the space may keep a flat state irrespective of the blanket by the floor board 1900 if the floor board 1900 exists, and thus the space where the urine/feces is collected may be adequately secured. To perform this function, the floor board 1900 should be stably fixed. Accordingly, the floor board 1900 may have a structure that wings 1912 and 1914 are formed at both sides of a body 1910, wherein the wings 1912 and 1914 may be pressed down by a support or an expansion section. Of course, a part of the body 1910 may be pressed down by the support or the expansion section. In this case, the floor board 1900 is pressed down by the patient, and thus the floor board 1900 may be stably fixed and keep level with a floor. Here, the body 1910 may locate in a space between a side members 1932 and 1934 of a support with a shape of "⊏" and the wings 1912 and 1914 may be pressed down by the side members 1932 and 1934.

On the other hand, the floor board 1900 may locate between the support and the expansion section.

In another embodiment, hole or a transparent part 2000 may be formed at a part of the floor board 1900 or a part on which the feces falls as shown in FIG. 20. It is desirable to form the transparent part 2000 considering falling of the feces. The hole or the transparent part 2000 is for sensing the feces. Particularly, a light emitting section and a light receiving section may be symmetrically disposed based on the floor board 1900 in the diaper. A light outputted form the light emitting section may be incident to the light receiving section through the transparent part 2000 and the light receiving section may transmit a sensed result to an external device. The transparent part 2000 keeps a transparent state when the feces is not outputted or the urine is discharged, but it has an opaque state when the feces is outputted. The feces may be detected by using this difference. Of course, an opaque part of the transparent part 2000 will be again transparent when the transparent part 200 is cleaned.

On the other hand, the other part of the floor board 1900 except the transparent part 2000 may be opaque.

While the floor board 1900 exists, the support and the expansion section may locate inside the first sub diaper 610 and the floor board 1900 may locate below the expansion section inside the first sub diaper 610, or the support may locate inside the first sub diaper 610, the expansion section may locate in the second sub diaper 612 and the floor board 1900 may locate below the support in the first sub diaper 610.

In another embodiment, in the event that the support and the expansion section locate in the second sub diaper 612, the floor board 1900 may locate inside the first sub diaper 610 or below the support and the expansion section in the second sub diaper 612.

On the other hand, the light emitting section and the light receiving section may be symmetrically disposed based on the floor board 1900 and a part of the first sub diaper 610 may be transparent so that a light passes through the transparent part. However, the light emitting section and the light receiving section may locate together over a side of the floor board 1900. In this case, a reflective part not the transparent part 2000 may be formed on the floor board 1900.

A sunlight panel for generating electricity when the light receiving section senses a light may be further formed in the diaper.

Furthermore, it may be measured that a part stained with the feces is wide or narrow if plural transparent parts are formed with separated on the floor board 1900 and the diaper, and thus amount of the feces may be roughly measured. Of course, since amount of the light passing through the transparent part 2000 is different depending on concentration of the feces, quality of the feces may be also measured through the amount of the light. In this case, a light emitting section or plural light emitting sections may be employed.

On the other hand, the transparent part of the diaper may be made up of transparent material, or hole may be formed on the diaper and a transparent member, e.g. transparent plastic plate may be adhered on a part including the hole.

In another embodiment, a transparent part may be formed at a part of the diaper without the floor board, and a light emitting section and a light receiving section may be symmetrically formed based on the transparent part to sense the feces. Of course, a reflector may be formed at a part of the diaper and the feces may be sensed by using reflection of the light. Here, a light emitting section and a light receiving section may locate in the same direction based on the reflector. In this case, an illumination sensor or a sunlight sensor may be used as the light receiving section.

The floor board is an integral structure, but plural sub floor boards may exist. The sub floor boards may be sequentially disposed. In this case, the sub floor boards may naturally support the hip of a user when the user lies on the bed and is seated.

Figure 21:
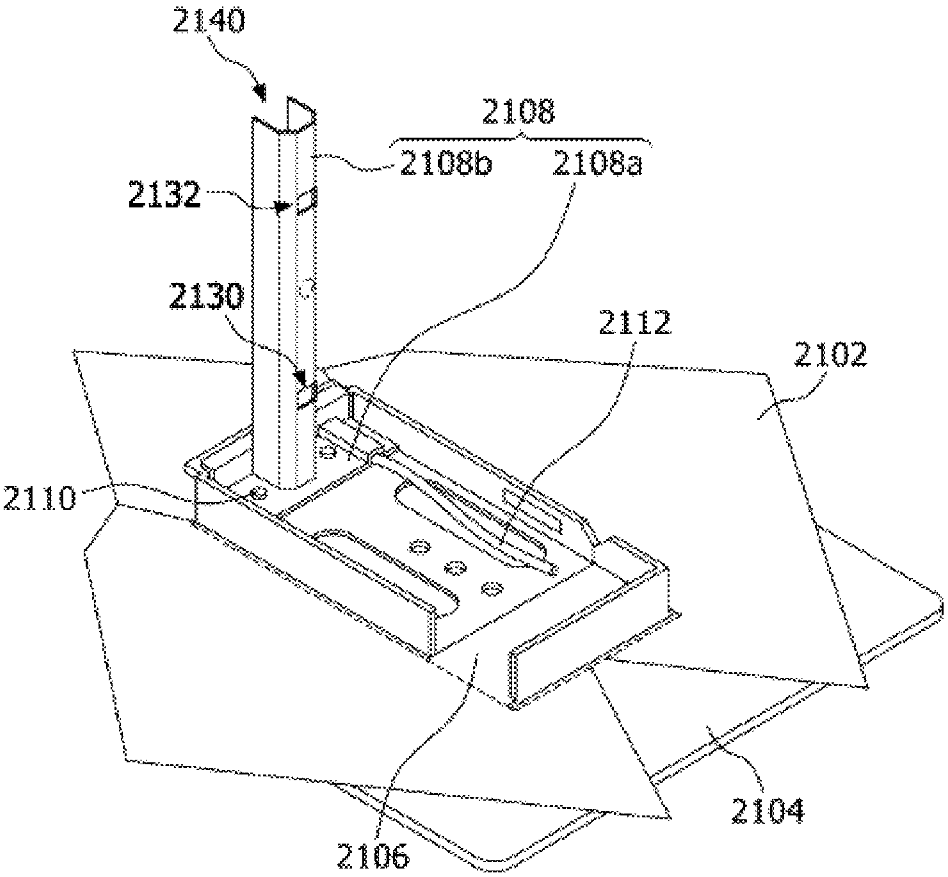
FIG. 21 is a view illustrating schematically a part of pants for urine/feces according to an embodiment of the disclosure.
Figure 21:
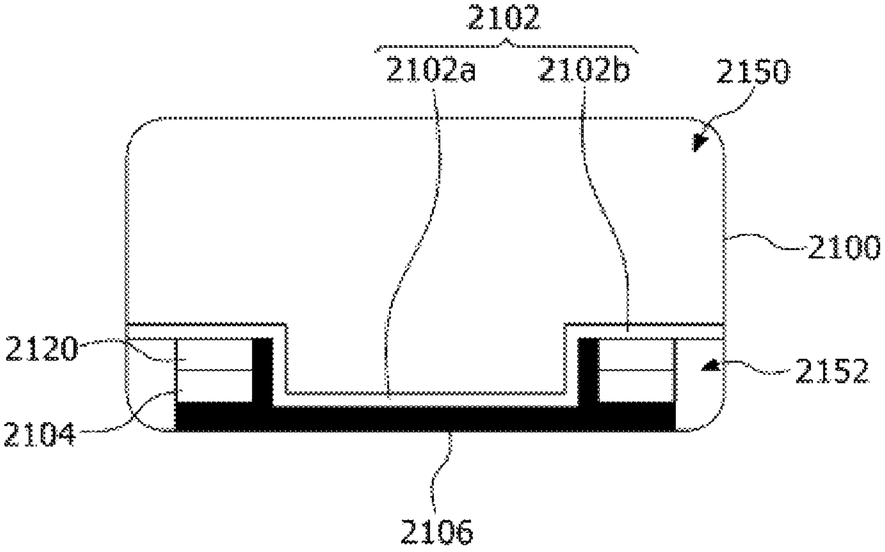
Figure 22:
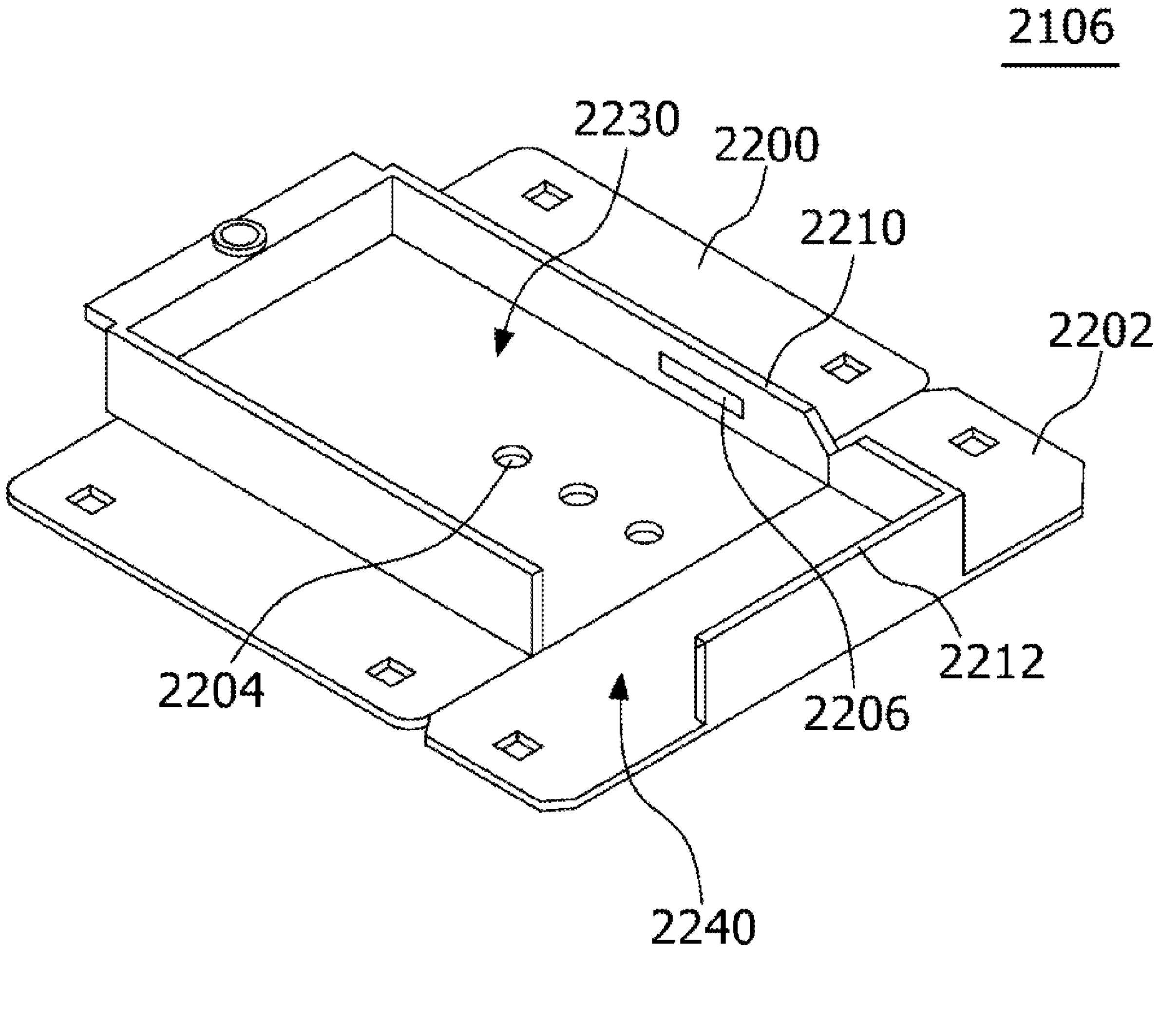
FIG. 22 is a view illustrating a top surface of a floor board according to another embodiment of the disclosure.
Figure 23:
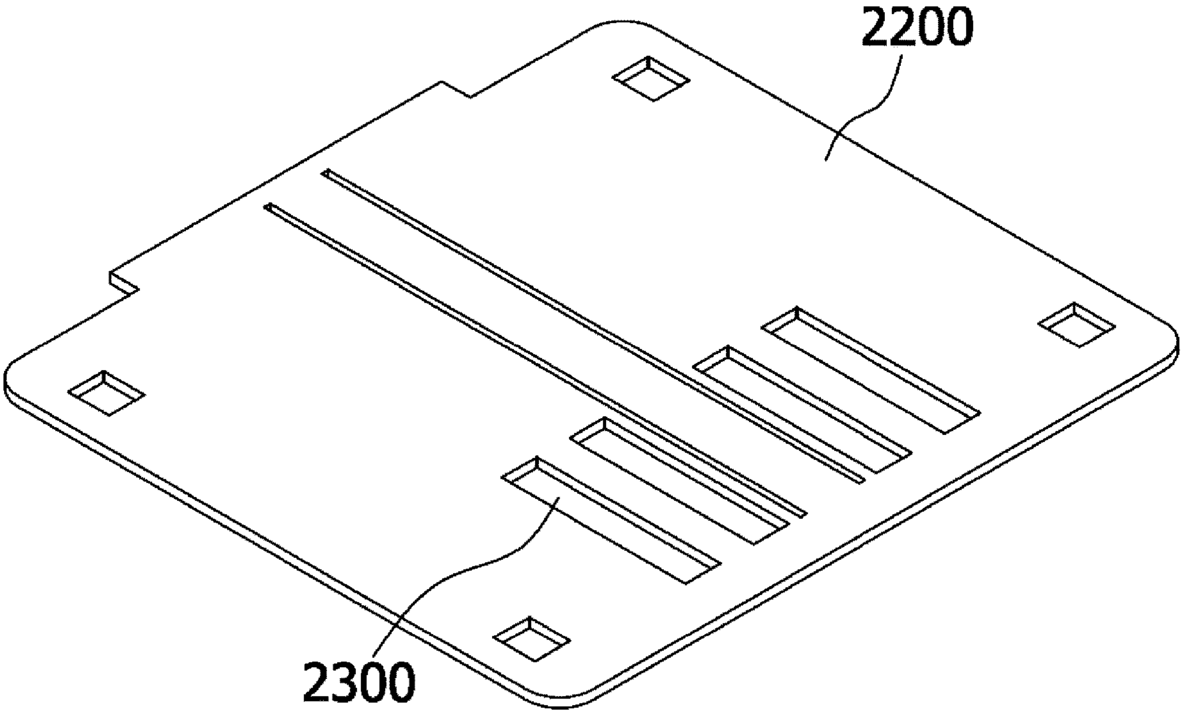
FIG. 23 is a view illustrating a lower surface of the floor board in FIG. 22.
Figure 24:
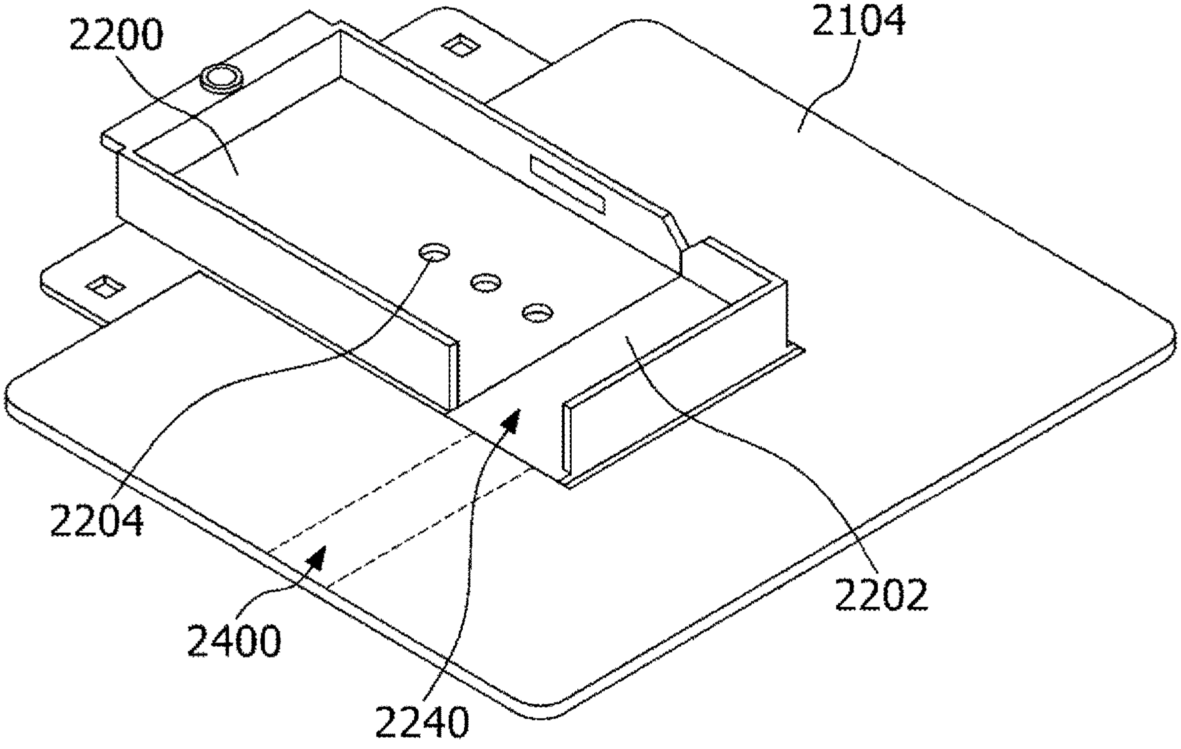
FIG. 24 is a view illustrating a structure that a support locates on a floor board according to an embodiment of the disclosure.
Figure 25:
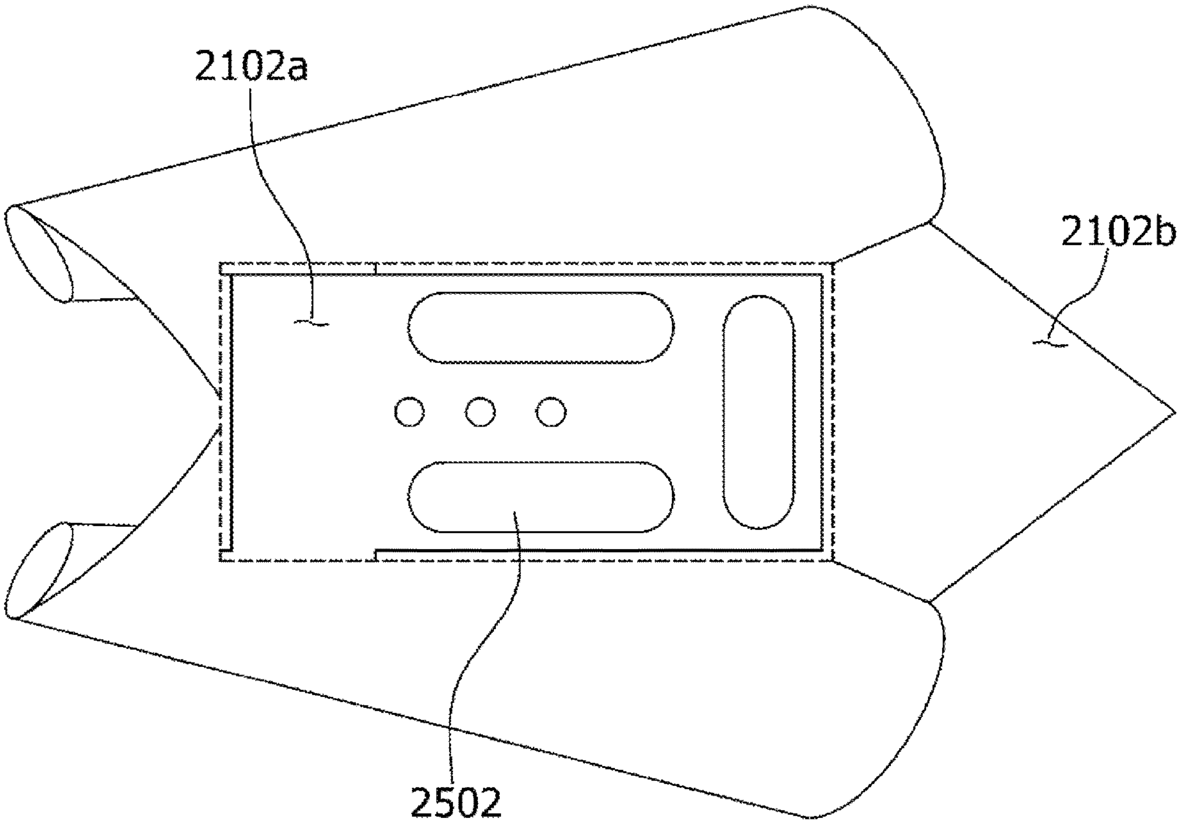
FIG. 25 is a view illustrating schematically a contact point of a second sub diaper and a part of a first sub diaper or the first sub diaper.
Figure 26:
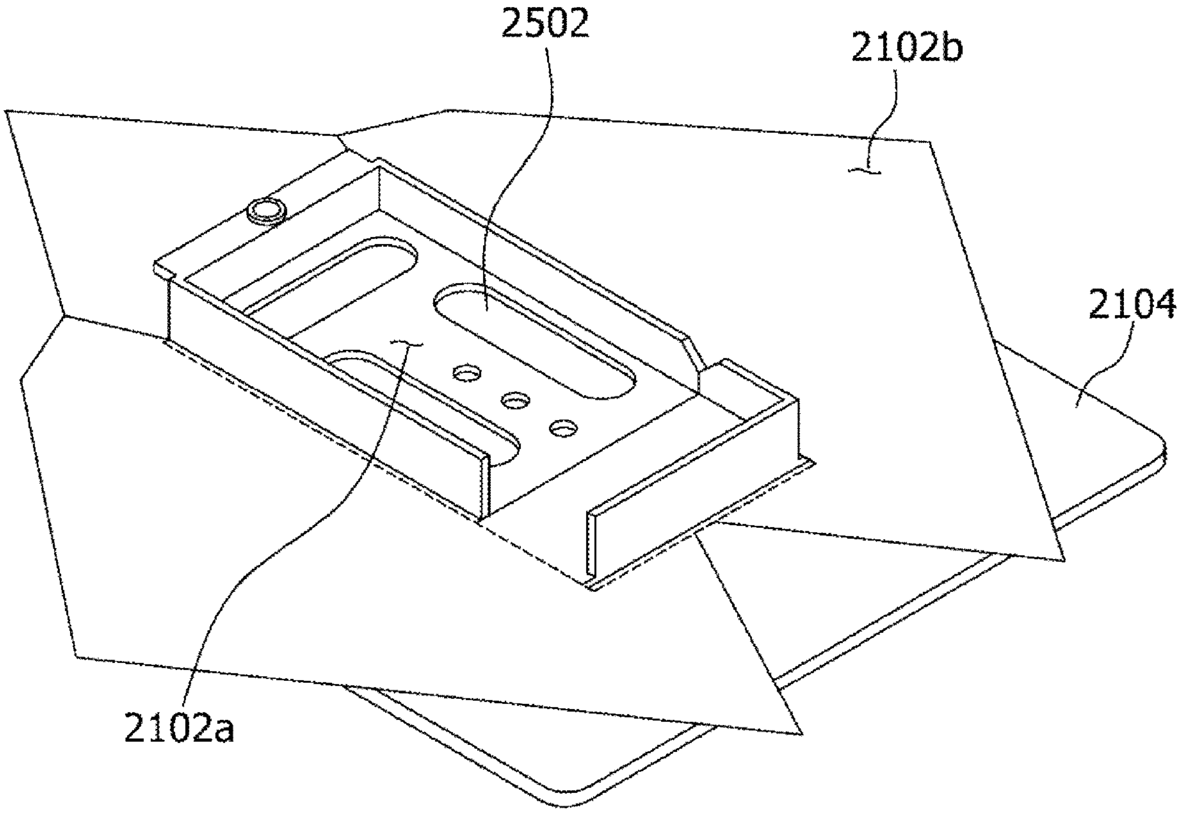
FIG. 26 to FIG. 27 are views illustrating schematically an array of a support, a floor board and a set structure according to an embodiment of the disclosure.
Figure 27:
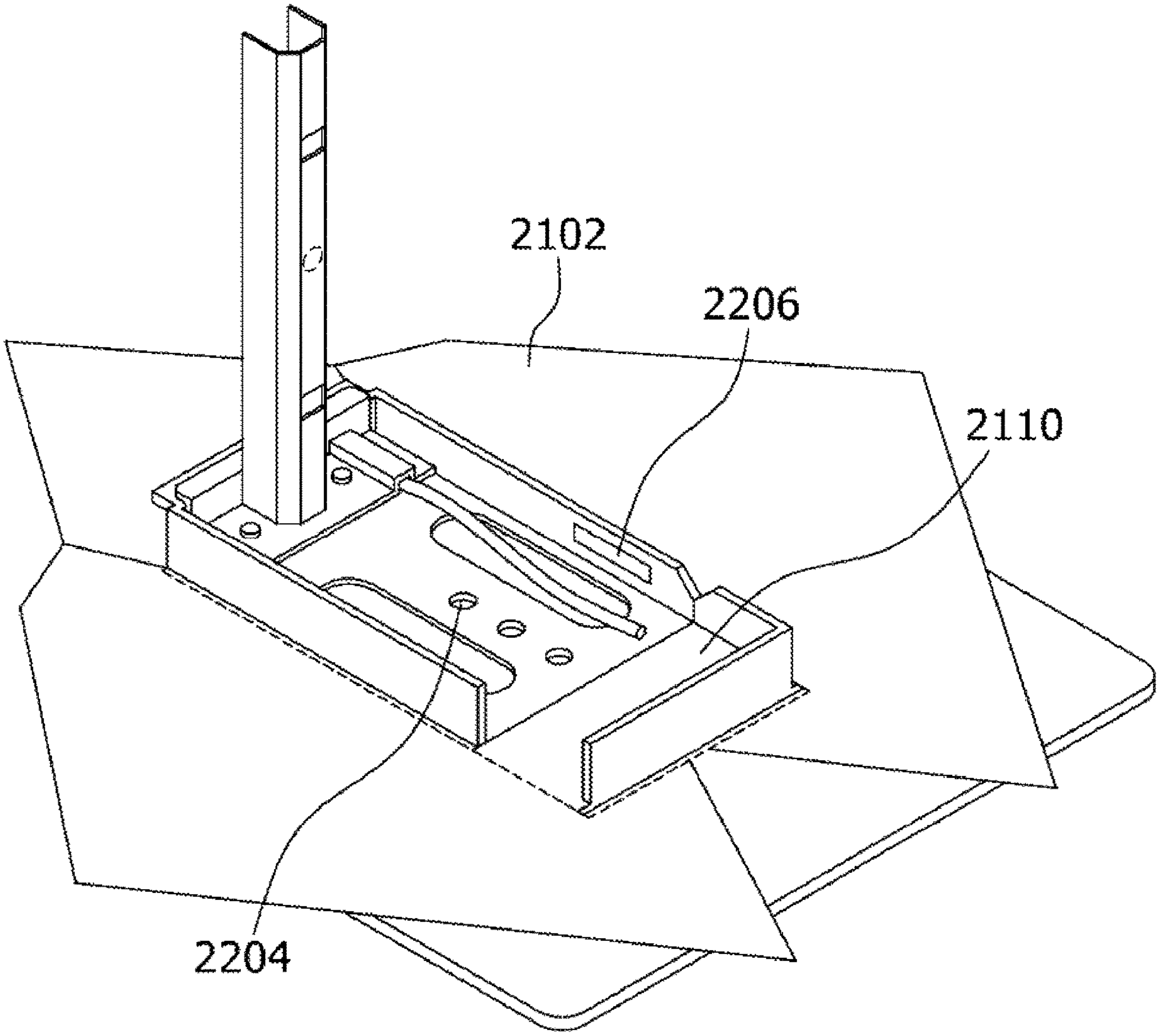
Figure 28:
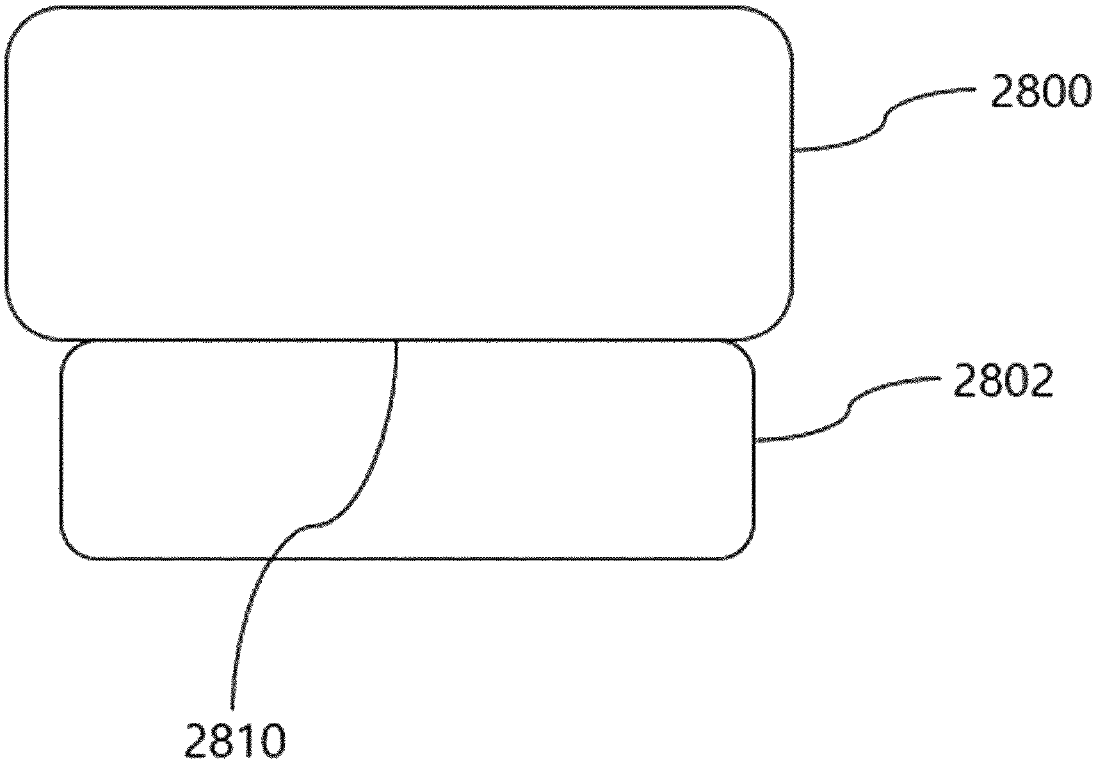
FIG. 28 is a view illustrating conceptually pants for urine/feces according to still another embodiment of the disclosure.
Figure 29:
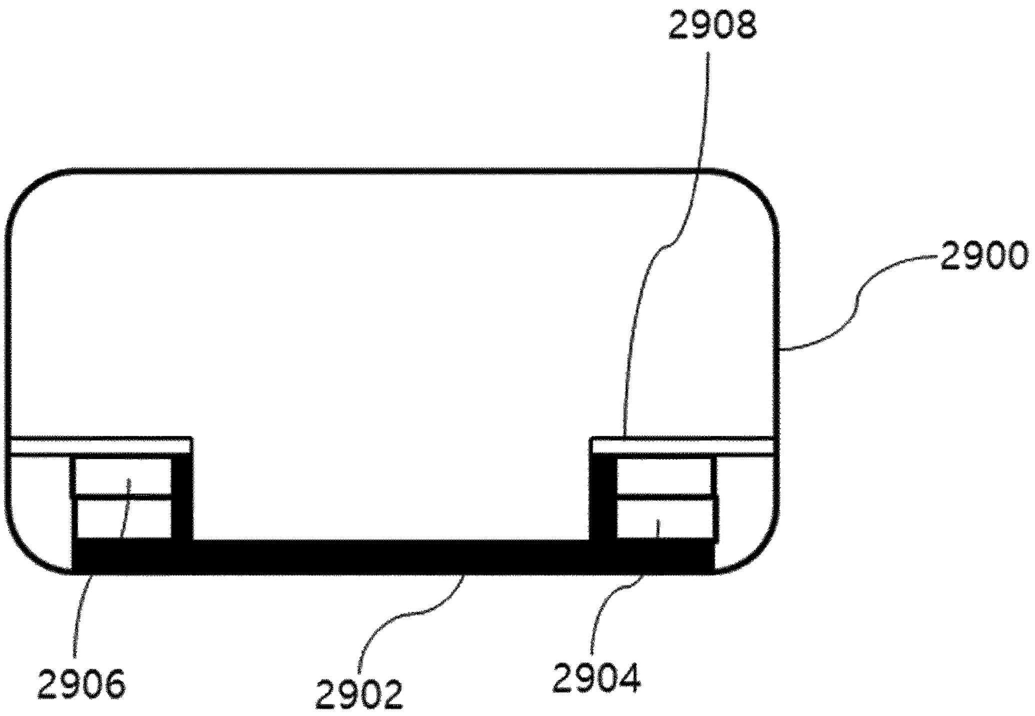
FIG. 29 is a view illustrating conceptually pants for urine/feces according to still another embodiment of the disclosure.

FIG. 21 is a view illustrating schematically a part of pants for urine/feces according to an embodiment of the disclosure, FIG. 22 is a view illustrating a top surface of a floor board according to another embodiment of the disclosure, and FIG. 23 is a view illustrating a lower surface of the floor board in FIG. 22. FIG. 24 is a view illustrating a structure that a support locates on a floor board according to an embodiment of the disclosure, FIG. 25 is a view illustrating schematically a contact point of a second sub diaper and a part of a first sub diaper or the first sub diaper, and FIG. 26 to FIG. 27 are views illustrating schematically an array of a support, a floor board and a set structure according to an embodiment of the disclosure. FIG. 28 is a view illustrating conceptually pants for urine/feces according to still another embodiment of the disclosure, and FIG. 29 is a view illustrating conceptually pants for urine/feces according to still another embodiment of the disclosure.

The pants for urine/feces of the disclosure may have two types of structures.

In a first structure, pants for urine/feces may have a structure that a space division member 2102 is formed in a pants member 2100 as shown in FIG. 21. Here, the pants may include a first space 2150 over the space division member 2102 and a second space 2152 below the space division member 2102. A user's hip, etc. may be inserted in the first space 2150, and a support 2104, an expansion section 2120 and a floor board 2106 may be included in the second space 2152. Here, the expansion section 2120 may locate below or over the support 2104, and the floor board 2106 may be formed of plastic.

The space division member 2102 may be adhered to the pants member 2100 and be removable from the pants member 2100. As a result, only the space division member 2102 may be separated after the urine/feces is disposed of, separated space division member 2102 may be cleaned, and then the cleaned space division member 2102 may be adhered to the pants member 2100 to be reused. That is, it can keep the pants clean through only cleaning of the space division member 2102.

In a second structure, pants for urine/feces may include a first sub pants 2800 where a hip and thighs are inserted and a second sub pants 2802 connected to the first sub pants 2800. Here, a support 2104, an expansion section 2120 and a floor board 2106 may be included in the second sub pants 2802. The expansion section 2120 may locate below or on the support 2104.

Here, an internal space of the first sub pants 2800 may correspond to the first space 2150 in the first structure, and an internal space of the second sub pants 2802 may correspond to the second space 2152 in the first structure.

Hereinafter, the structure and an operation of the pants in the first structure will be described in detail. An operation of the second structure is similar to an operation of the first structure, except that a contact part of the second sub pants 2802 and a lower surface of the first sub pants 2800 or the first sub pants 2800 is formed of transparent substance.

In the second space 2152, the support 2104 and the expansion section 2120 may be disposed on the floor board 2106.

In an embodiment, the floor board 2106 may include a first sub floor board 2200 and a second sub floor board 2202 separated each other as shown in FIG. 22. In this case, the user feels convenience when the user is seated as well as when the user is lay. Of course, two sub floor boards 2200 and 2202 are used in above description, but three or more sub floor boards may be used. The floor board 2106 may be combined with a lower surface of the pants member 2100 or a lower surface of the second sub pants 2802.

In an embodiment, a vertical member 2210 may be formed with a shape of "⊏" on the first sub floor board 2200, and a vertical member 2212 may be formed with a shape of '¬' on the second sub floor board 2202. Here, facing parts of the vertical members 2210 and 2212 may be disposed side by side. As a result, a space 2230 may be formed by the vertical member 2210 and 2212 as shown in FIG. 21. Hole 2240 may be formed at a part of the space 2230 formed by the vertical members 2210 and 2212. The hole 2240 corresponds to a discharge path through which urine/feces flows.

The support 2104 with the shape of '⊏' may be disposed on the floor board 2106 as shown in FIG. 24. For example, the support 2104 may be disposed outside the vertical members 2210 and 2212 along the vertical members 2210 and 2212 on the floor board 2106. That is, the support 2104 may surround the vertical members 2210 and 2212. Particularly, a part corresponding to the hip section of the support 2104 may be disposed on the second sub floor board 2202, and a part corresponding to the thigh of the support 2104 may be disposed on the second sub floor board 2202 and the first sub floor board 2200.

The expansion section 2120 may be disposed on the support 2104 while the support 2104 locates on the floor board 2106. A structure that the support 2104 and the expansion section 2120 locate on the floor board 2106 is disposed in the second space 2152 and the hip and the thigh of the user is included in the first space 2150, and thus the hip or the thigh in the first space 2150 may be lifted when the expansion section 2120 is expanded. Here, the floor board 2106 and the support 2104 keep original state though the expansion section 2120 is expanded.

In an embodiment, a hip expansion section and a thigh expansion section may exist, the hip expansion section may locate on or below the support 2104 in the second space 2152, and the thigh expansion section may locate on a part corresponding to the thigh while it locates outside the pants for urine/feces. Here, a thigh support may locate in the pants.

Of course, the thigh expansion section may locate in the second space 2152 of the pants, but it is efficient that the thigh expansion section locates outside the pants because the thigh expansion section can raise adequately the thigh. The thigh may not be adequately lifted though the thigh expansion section is expanded if the thigh expansion section locates in the pants. However, the thigh may be adequately lifted if the thigh expansion section locates outside the pants. As a result, collected urine/feces may be well discharged.

In another embodiment, the expansion section 2120 locates on the first support 2104. A second support (sub support) as additional element may be disposed on the expansion section 2120 in the second space 2152. The second support can support conveniently the user's hip. To perform this function, strength of the second support is smaller than that of the first support 2104 or the second support may have an embossing structure. That is, the first support 2104 may be hard support and the second support may be soft support.

In still another embodiment, a second support may be included in the expansion section 2120 located on the first support 2104. The second support can support softly the user's hip while the expansion section 2120 is not expanded. Here, strength of the second support may be smaller than that of the first support 2104.

In still another embodiment, supports may locate respectively on and below the expansion section 2120, and another support may be included in the expansion section 2120.

In still another embodiment, a second support and an expansion section may locate sequentially on the first support. Here, strength of the second support may be smaller than that of the first support.

That is, additional support may exist on, below or in the expansion section 2120, and a strength or substance of the supports may differ.

On the other hand, the pants for urine/feces according to the disclosure may sense urine/feces by using a light sensor. Particularly, at least one light receiving section 2204 may exist in the space 2230 formed by the vertical member 2210 of the first floor board 2200 as shown in FIG. 22, and the space division member 2102 may include a transparent section 2102*a* and a connection section 2102*b* as shown in FIG. 21 and FIG. 25. In the second structure, a contact part of the first sub pants 2800 and the second sub pants 2802 or a part corresponding to the space 2230 of the first sub pants 2800 may be formed of transparent material so that a light passes.

The transparent part 2102*a* of the space division member 2102 or the transparent part of the first sub pants 2800 may correspond to the space 2230 formed by the vertical members 2210 and 2212 of the floor board 2200.

In an embodiment, a light emitting section 2206 may be formed on the vertical member 2210 of the first sub floor board 2200 as shown in FIG. 22 and FIG. 27. As a result, a light emitted from the light emitting section 2206 may be transmitted to the first space 2150 through the transparent part 2102*a*, and then the transmitted light may be incident to the light receiving section 2204 in the second space 2152 through the transparent part 2102*a*. Amount of the light incident to the light receiving section 2204 is small if the feces exists on the transparent part 2102*a*. That is, discharge of the feces, concentration of the feces, etc. may be detected by using the light sensor.

As shown in FIG. 24, light receiving sections 2204 may be sequentially disposed with separated on the first sub floor board 2200 to detect approximately amount of the feces. It means that amount of the feces is much if a light is not received or received a little to three light receiving sections 2204 in FIG. 24, and it means that amount of the feces is small if a light is received a little to only one light receiving section 2204.

In another embodiment, a reverse T type set structure 2108 may be disposed on the first sub floor board 2200 in the first space 2150 as shown in FIG. 21. Here, a light emitting section (dotted part) may be formed on the set structure 2108. As a result, a light outputted from the light emitting section may be incident to the light receiving section 2204 through the transparent part 2102*a*.

In still another embodiment, the light emitting section may locate outside the pants for urine/feces, and the light receiving section may locate inside the pants. Here, a transparent part may be formed at the pants so that the light outputted from the light emitting section is incident in the pants through the transparent part. That is, the light outputted from the light emitting section may be received to the light receiving section after passing through the urine/feces or reflected from the urine/feces in the pants. Accordingly, the output of the urine/feces by the user may be sensed.

In still another embodiment, the light emitting section and the light receiving section may locate outside the pants for urine/feces. In this case, a first transparent part through which the light outputted from the light emitting section is incident and a second transparent part through which the light passing through the urine/feces or reflected by the urine/feces passes may be formed at the pants.

The set structure 2108 may include a bottom section 2108*a* and a support section 2108*b*. Here, the bottom section 2108*a* may be disposed on the first sub floor board 2200, and the support section 2108*b* may cross over the bottom section 2108*a*, preferably be vertical to the bottom section 2108*a*.

In an embodiment, a space 2140 in which a floor cleaning pipe and a human body cleaning pipe are received may be formed at a back side of the support section 2108*b*, holes 2130 and 2132 may be respectively at a lower part and an upper part of a front side of the support section 2108*b*, at least one first nozzle 2110 may be formed on the bottom section 2108*a*, and a second nozzle 2112 may be exposed outside through the bottom section 2108*a*.

The first nozzles 2110 and the second nozzle 2112 may be connected to the floor cleaning pipe inserted into the space 2140 of the back side of the support section 2108*b*, respectively. As a result, the urine/feces moves in a front direction if water is spouted through the first nozzles 2110, and it shifts the urine/feces in a side direction if water is spouted through the second nozzle 2112.

In an embodiment, hole may be formed at a part (dotted line in FIG. 25) of the transparent part 2102*a* of the space division member 2102, and hole 2400 may be formed through the support 2104 corresponding to the hole. The hole and the hole 2400 correspond to the hole 2240 formed at a part of the space 2230 formed by the vertical members 2210 and 2212. As a result, the urine/feces shifted by the nozzles 2110 and 2112 may be discharged outside through the hole of the transparent part 2102*a*, the hole 2400 of the support 2104 and the discharge pipe. Here, the discharge pipe may be connected to the pants member 2100 at a part corresponding to the hole 2400 of the support 2104.

A first human body nozzle connected to the human body cleaning pipe inserted in the space 2140 of the back side of the support section 2108*b* may be formed at the lower part of the support section 2108*b*, and a second human body nozzle connected to the human body cleaning pipe may be formed at the hole 2132 formed at the upper part of the support section 2108*b*. The first human body nozzle may clean the user's hip, and the second human body nozzle may clean genitals.

In an embodiment, whole or the upper part of the support section 2108*b* may be formed of flexible material. This is for keeping stably the support section 2108*b* irrespective of user's posture.

In an embodiment, a light emitting section may be established at a front side of the support section 2108*b*, for example the light emitting section may be formed between holes 2130 and 2132 as shown in a dotted line in FIG. 21. A light emitted from the light emitting section may be incident to the light receiving section 2204 located on the first sub floor board 2200 through the transparent part 2102*a* of the space division member 2102 or a transparent part of a lower side of the first sub pants 2800. In this case, the light receiving section 2206 formed on the vertical member 2210 of the first sub floor board 2200 may not exist.

In an embodiment, a metal member 2502 may be included in the transparent part 2102*a* of the space division member 2102 as shown in FIG. 25, and a magnet may be formed on the floor board 2106, e.g. a bottom of the first sub floor board 2200 as shown in FIG. 23. As a result, the transparent part 2102*a* of the space division member 2102 may be stably close to the space 2230 of the floor board 2106.

Of course, another method not the method of using the magnet may be used as long as the transparent part 2102*a* is stable close to the floor board 2106. For example, at least partial of the transparent part 2102*a* may be inserted into a groove of the floor board 2106, or the transparent part 2102*a* may be adhered to the floor board 2106.

On the other hand, the transparent part 2102*a* is formed at the space division member 2102 or the part of the first sub pants 2800 is transparent in the above description, but a transparent part may not exist to the space division member 2102 and the first sub pants 2800. In this case, the urine/feces may not be detected by using the light sensor but be sensed by another method, e.g. a weight sensor, etc. Of course, the light sensor may be used by forming hole to the space division member 2102.

The space division member 2102 is used in the above description. However, a space may exist in a pants member 2900 without the space division member as shown in FIG. 29, and a floor board 2902, a support 2904, an expansion section 2906 and user's hip, etc. may be included in the space. For example, connection members 2908, e.g. fabric formed at both internal terminals of the pants member 2900 may be connected to vertical members of a floor board 2902, but a transparent part does not exist in the floor board 2902. That is, the connection member 2908 connected to an internal surface of the pants member 2900 exists, but the connection member 2908 does not divide completely the internal space of the pants member 2900 into two spaces. In this case, urine/feces is stacked in a space formed by vertical members of the floor board 2902. Of course, a light sensor and a set structure are similar in the embodiments described above.

For example, the floor board 2902 may include a first sub floor board and a second sub floor board separated each other. The first sub floor board and the second sub floor board may be sequentially disposed, vertical members may be respectively formed on the first sub floor board and the second sub floor board, specific space may be formed by the vertical members, and a support 2904 may surround the vertical members.

Additionally, at least one light receiving section may be formed on the first sub floor board and a light emitting section may be formed on one of the vertical members of the sub floor boards. A light outputted form the light emitting section may be incident to the light receiving section, and the urine/feces may be sensed through emitting/receiving of the light.

Furthermore, a set structure disposed on the floor board 2902 may include a bottom section and a support section crossing over the bottom section, a floor cleaning pipe may be inserted into a space of a back side of the support section, a first nozzle connected to the floor cleaning pipe may be formed at the bottom section, and a second nozzle connected to the floor cleaning pipe may be exposed outside through the bottom section. In this case, wash water outputted from the first nozzle may transfer the urine/feces on the floor board 2902 in a front direction, wash water outputted from the second nozzle moves the urine/feces on the floor board 2902 in a side direction, and the urine/feces may be discharged outside through hole of the support 2904 and a discharge pipe.

Components in the embodiments described above can be easily understood from the perspective of processes. That is, each component can also be understood as an individual process. Likewise, processes in the embodiments described above can be easily understood from the perspective of components.

What is claimed is:

1. A pants for urine/feces comprising:

a pants member configured to have an internal space;

a space division member connected to the pants member in the internal space, thereby dividing the internal space into a first space and a second space;

an expansion section disposed in the second spaces; and a floor board disposed in the second space, wherein a hip of a user or the hip and a thigh locate in the first space, the hip or the hip and the thigh are lifted when the expansion section is expanded in the second space to form a space for urine/feces where the urine/feces is collected, wherein a support and the expansion section locate on the floor board, the space division member includes a transparent part and a connection part, and wherein the floor board includes a first sub floor board and a second sub floor board separated with each other, vertical members are respectively formed on the first sub floor board and the second sub floor board, a specific space is formed by the vertical members, the support surrounds the vertical members, and the transparent part corresponds to the specific space;

wherein at least one light receiving section is formed on the first sub floor board, and a light emitting section is formed on one of the vertical members, and wherein a light emitted from the light emitting section is incident to the light receiving section through the transparent part, and discharging of the urine/feces is sensed through emitting and receiving of the light.

2. The pants of claim 1, further comprising:

a support disposed on or below the expansion section in the second space, wherein the space division member is removable from the pants member.

3. The pants of claim 1, wherein the light receiving sections are sequentially disposed on the first sub floor board, and wherein the light emitted from the light emitting section is incident to the light receiving section through the transparent part, and amount of the urine/feces as well as the discharging of the urine/feces is detectable by using the emitting and receiving of the light.

4. The pants of claim 1, wherein a metal member is included in the transparent part, a magnet is formed on the floor board, and the transparent part is closed to the floor board by the metal member and the magnet.

5. The pants of claim 1, further comprising:

a set structure disposed on the floor board in the first space, wherein the set structure includes a bottom section and a support section crossing over the bottom section, a floor cleaning pipe and a human body cleaning pipe are inserted in a space of a back side of the support section, a first nozzle connected to the floor cleaning pipe is formed on the bottom section, a second nozzle connected to the floor cleaning pipe is exposed outside through the bottom section, hole is formed at a part of the transparent part, hole is formed on the support, wash water outputted from the first nozzle moves urine/feces in the space of the urine/feces in a front direction, wash water outputted from the second nozzle moves the urine/feces in the space for the urine/feces in a side direction, the moved urine/feces is discharged outside through the hole of the transparent part, the hole of the support and a discharge pipe, hole is formed on the support section, a third nozzle connected to the human body cleaning pipe is inserted in the hole of the support section, and wash water outputted from the third nozzle cleans the hip of the user.

6. The pants of claim 5, wherein a light emitting section is formed on the support section and a light receiving section is formed on the bottom section, and wherein a light outputted from the light emitting section is incident to the light receiving section through the transparent part, the discharging of the urine/feces is sensed through emitting and receiving of the light, and whole or an upper part of the support section is formed of flexible material.

7. The pants of claim 1, further comprising:

a discharge pipe configured to discharge outside the urine/feces collected in the space for the urine/feces, wherein a urine sensor exists in the discharge pipe, and the collected urine is automatically discharged outside when the urine sensor senses the urine.

8. The pants of claim 1, further comprising:

a cleaning pipe connected to the pants member, wherein the collected urine/feces is collected to a collection section through a discharge pipe, the cleaning pipe is connected to a wash water section, wash water is supplied from the wash water section to the cleaning pipe, a weight sensor locates below the wash water section or the collection section, an alarm is provided to a manager when it is sensed through the weight sensor that amount of the wash water of the wash water section is less than a preset value or amount of the urine/feces or contaminated water in the collection section is more than a predetermined level.

9. The pants of claim 1, wherein a box in which a pump is included exists, and wherein a fan is established to the box, the collected urine/feces is discharged outside through a discharge pipe, air in the pants of the urine/feces is inhaled through the discharge pipe in response to rotation of the fan, the inhaled air is outputted outside through the fan, the fan rotates more slowly when the urine/feces is not disposed of as opposed to when the urine/feces is collected through the discharge pipe, and rotation velocity of the fan when the urine/feces is collected is greater than rotation velocity of the fan when the urine/feces is not collected.

10. The pants of claim 9, wherein a temperature sensor for measuring temperature of the air inhaled by the fan exists, and wherein the rotation velocity of the fan gets rapider as the measured temperature is high.

11. The pants of claim 9, wherein hole is formed on the box, and wherein the hole is opened/closed, the hole is opened when the collected urine/feces is discharged outside through the discharge pipe, and the hole is closed otherwise.

12. The pants of claim 1, wherein a first support, the expansion section and a second support exist in the second space, and another expansion section locates outside the pants for urine/feces, and wherein the expansion section lifts the hip with located on or below the first support, the first support and the another expansion section correspond to a thigh of the user, and the thigh is lifted when the another expansion section is expanded.

13. The pants of claim 1, wherein a first support locates below the expansion section in the second space, and a second support locates on the expansion section.

14. The pants of claim 1, wherein the expansion section locates on a first support in the second space, and wherein a second support exists in the expansion section.

15. A pants for urine/feces comprising:

a pants member configured to have an internal space;

an expansion section disposed in the pants member;

a light sensor located in the pants, wherein a hip or the hip and a thigh of a user is lifted when the expansion section is expanded, thereby forming a space for collecting the urine/feces, wherein the light sensor includes a light emitting section and a light receiving section, the light emitting section outputs a light in a direction of the urine/feces, and wherein the light receiving section of the light sensor senses a light reflected by the collected urine/feces or contaminated water or a light through the collected urine/feces or the contaminated water to detect whether or not the user discharges the urine/feces.

16. The pants of claim 15, wherein the light emitting section of the light sensor locates outside the pants member and the light receiving section of the light sensor locates in the pants member, and wherein a transparent part through which a light outputted from the light emitting section passes is formed on the pants member.

17. The pants of claim 15, further comprising:

a support and a floor board located in the pants member, wherein the support and the expansion section are disposed on the floor board or the expansion section.

18. The pants of claim 17, wherein the floor board includes a vertical member, a specific space is formed on the floor board by the vertical member, the vertical member is connected to an internal surface of the pants member through a connection member, the support surrounds the vertical member, and the urine/feces is collected in the specific space of the floor board.

19. The pants of claim 18, wherein the floor board includes a first sub floor board and a second sub floor board separated each other, and wherein the first sub floor board and the second sub floor board are sequentially disposed, vertical members are respectively formed on the first sub floor board and the second sub floor board, the specific space is formed by the vertical members, and the support surrounds the vertical members.

20. The pants of claim 19, wherein at least one light receiving section is formed on the first sub floor board, and a light emitting section is formed on one of the vertical members of the sub floor boards, and wherein a light emitted from the light emitting section is incident to the light receiving section, and discharging of the urine/feces is sensed through emitting and receiving of the light.

21. The pants of claim 18, further comprising:

a set structure disposed on the floor board, wherein the set structure includes a bottom section and a support section crossing over the bottom section, a floor cleansing pipe is inserted in a space of a back side of the support section, a first nozzle connected to the floor cleaning pipe is formed on the bottom section, a second nozzle connected to the floor cleaning pipe is exposed outside through the bottom section, wash water outputted from the first nozzle moves urine/feces on the floor board in a front direction, wash water outputted from the second nozzle moves the urine/feces on the floor board in a side direction, the moved urine/feces is discharged outside through hole of the support and a discharge pipe.

22. The pants of claim 15, wherein a first support, the expansion section and a second support are included in the pants member, another expansion section locates outside the pants member for urine/feces, and wherein the expansion section lifts the hip with located on or below the first support, the first support and the another expansion section correspond to the thigh of the user, and the thigh is lifted when the another expansion section is expanded.

23. The pants of claim 15, wherein a first support locates below the expansion section in the internal space, and a second support locates on the expansion section.

24. The pants of claim 15, wherein the expansion section locates on a first support in the internal space, and wherein a second support exists in the expansion section.

* * * * *